US008476022B2

(12) United States Patent
Ronaghi et al.

(10) Patent No.: US 8,476,022 B2
(45) Date of Patent: Jul. 2, 2013

(54) METHOD OF MAKING AN ARRAY OF NUCLEIC ACID COLONIES

(75) Inventors: Mostafa Ronaghi, San Diego, CA (US); Helmy A. Eltoukhy, Woodside, CA (US)

(73) Assignee: Illumina, Inc., San Diego, CA (US)

( * ) Notice: Subject to any disclaimer, the term of this patent is extended or adjusted under 35 U.S.C. 154(b) by 0 days.

(21) Appl. No.: 13/545,682

(22) Filed: Jul. 10, 2012

(65) Prior Publication Data

US 2012/0295262 A1    Nov. 22, 2012

Related U.S. Application Data

(63) Continuation of application No. 12/641,104, filed on Dec. 17, 2009, now Pat. No. 8,236,532.

(60) Provisional application No. 61/140,566, filed on Dec. 23, 2008.

(51) Int. Cl.
*C12Q 1/68* (2006.01)
*C12P 19/34* (2006.01)

(52) U.S. Cl.
USPC ................................ 435/6.12; 435/91.2

(58) Field of Classification Search
USPC ............................... 435/6.12, 91.2
See application file for complete search history.

(56) References Cited

U.S. PATENT DOCUMENTS

| | | | |
|---|---|---|---|
| 4,971,903 A | 11/1990 | Hyman et al. | |
| 5,302,509 A | 4/1994 | Cheeseman | |
| 5,405,747 A | 4/1995 | Jett et al. | |
| 5,641,658 A | 6/1997 | Adams et al. | |
| 5,830,655 A | 11/1998 | Monforte et al. | |
| 5,834,189 A | 11/1998 | Stevens et al. | |
| 5,976,802 A | 11/1999 | Ansorge et al. | |
| 5,981,186 A | 11/1999 | Gabe et al. | |
| 6,090,592 A | 7/2000 | Adams et al. | |
| 6,172,218 B1 | 1/2001 | Brenner | |
| 6,210,891 B1 | 4/2001 | Nyren et al. | |
| 6,258,568 B1 | 7/2001 | Nyren | |
| 6,274,320 B1 | 8/2001 | Rothberg et al. | |
| 6,306,597 B1 | 10/2001 | Macevicz | |
| 6,613,513 B1 | 9/2003 | Parce et al. | |
| 6,869,764 B2 | 3/2005 | Williams et al. | |
| 6,969,488 B2 | 11/2005 | Bridgham et al. | |
| 7,001,792 B2 | 2/2006 | Sauer et al. | |
| 7,033,764 B2 | 4/2006 | Korlach et al. | |
| 7,052,839 B2 | 5/2006 | Nelson et al. | |
| 7,057,026 B2 | 6/2006 | Barnes et al. | |
| 7,115,400 B1 | 10/2006 | Adessi et al. | |
| 7,211,414 B2 | 5/2007 | Hardin et al. | |
| 7,315,019 B2 | 1/2008 | Turner et al. | |
| 7,329,492 B2 | 2/2008 | Hardin et al. | |
| 7,361,466 B2 | 4/2008 | Korlach et al. | |
| 7,405,281 B2 | 7/2008 | Xu et al. | |
| 7,416,844 B2 | 8/2008 | Korlach et al. | |
| 7,427,673 B2 | 9/2008 | Balasubramanian et al. | |
| 7,767,400 B2 | 8/2010 | Harris | |
| 7,785,790 B1 | 8/2010 | Church et al. | |
| 7,985,565 B2 * | 7/2011 | Mayer et al. | 435/91.2 |
| 2002/0055100 A1 | 5/2002 | Kawashima et al. | |
| 2002/0115076 A1 | 8/2002 | Williams | |
| 2003/0036080 A1 | 2/2003 | Jensen et al. | |
| 2003/0087300 A1 | 5/2003 | Knapp et al. | |
| 2003/0108867 A1 | 6/2003 | Chee | |
| 2004/0002090 A1 | 1/2004 | Mayer et al. | |
| 2004/0096853 A1 | 5/2004 | Mayer | |
| 2005/0042648 A1 | 2/2005 | Griffiths et al. | |
| 2005/0053986 A1 | 3/2005 | Makarov et al. | |
| 2005/0079510 A1 | 4/2005 | Berka et al. | |
| 2005/0100900 A1 | 5/2005 | Kawashima et al. | |
| 2005/0130173 A1 | 6/2005 | Leamon et al. | |
| 2006/0024681 A1 | 2/2006 | Smith et al. | |
| 2006/0188901 A1 | 8/2006 | Barnes et al. | |
| 2006/0199193 A1 | 9/2006 | Koo et al. | |
| 2006/0240439 A1 | 10/2006 | Smith et al. | |

(Continued)

FOREIGN PATENT DOCUMENTS

| | | |
|---|---|---|
| GB | 2398383 | 8/2004 |
| WO | WO 90/04652 | 5/1990 |

(Continued)

OTHER PUBLICATIONS

International Preliminary Report on Patentability dated Jul. 7, 2011 for International Application No. PCT/US2009/068569, filed Dec. 17, 2009.
International Search Report and Written Opinion dated Sep. 10, 2010 for International Application No. PCT/US2009/068569, filed Dec. 17, 2009.
Adessi, et al., "Solid Phase DNA amplification: characterisation of primer attachment and amplification mechanisms", Nucleic Acids Research 28, 2000, 1-8.
Agah, et al., "A high-resolution low-power oversampling ADC with extended-range for bio-sensor arrays", IEEE Symposium, 2007, 244-245.
Ansorge, et al., "Automated DNA sequencing: ultrasensitive detection of fluorescent bands during electrophoresis", Nucleic Acids Research, 15(11), 1987, 4593-4602.

(Continued)

*Primary Examiner* — Kenneth Horlick
(74) *Attorney, Agent, or Firm* — John T. Murphy

(57) ABSTRACT

A method of making an array of nucleic acid colonies, by (a) providing a substrate having a patterned surface of features, wherein the features are spatially separated from each other on the surface of the substrate; (b) contacting the substrate with a solution of different target nucleic acids to seed a subset of the features that contact the solution, wherein each feature in the subset is seeded with a single nucleic acid from the solution, wherein a plurality of the features that contact the solution are not seeded with a nucleic acid from the solution; (c) amplifying the nucleic acids to form a nucleic acid colony at each of the features in the subset; and (d) repeating steps (b) and (c) to increase the number of the features on the surface that have a nucleic acid colony, thereby making an array of nucleic acid colonies.

19 Claims, 2 Drawing Sheets

U.S. PATENT DOCUMENTS

| | | | |
|---|---|---|---|
| 2006/0281109 | A1 | 12/2006 | Ost et al. |
| 2006/0292611 | A1 | 12/2006 | Berka et al. |
| 2007/0128624 | A1 | 6/2007 | Gormley et al. |
| 2007/0166705 | A1 | 7/2007 | Milton et al. |
| 2008/0009420 | A1 | 1/2008 | Schroth et al. |
| 2008/0108082 | A1 | 5/2008 | Rank et al. |
| 2010/0009871 | A1* | 1/2010 | Reed et al. ............. 506/26 |
| 2010/0075309 | A1 | 3/2010 | Maxham et al. |
| 2010/0120625 | A1 | 5/2010 | Weissman et al. |
| 2010/0279882 | A1 | 11/2010 | Ronaghi et al. |

FOREIGN PATENT DOCUMENTS

| | | |
|---|---|---|
| WO | WO 91/06678 | 5/1991 |
| WO | WO 92/02635 | 2/1992 |
| WO | WO 2004/018497 | 3/2004 |
| WO | WO 2005/010145 | 2/2005 |
| WO | WO 2005/065814 | 7/2005 |
| WO | WO 2005/078130 | 8/2005 |
| WO | WO 2006/064199 | 6/2006 |
| WO | WO 2007/010251 | 1/2007 |
| WO | WO 2007/010252 | 1/2007 |
| WO | WO 2007/123744 | 11/2007 |
| WO | WO 2008/041002 | 4/2008 |
| WO | WO 2010/075188 | 7/2010 |

OTHER PUBLICATIONS

Cockroft, et al., "A single-molecule nanpore device detects DNA polymerase activity with single-nucleotide resolution", J. Am. Chem. Soc, 130(3), 2008, 818-820.

Connell, et al., "Automated DNA Sequence Analysis", Biotechniques 5(4):342-348, 1987, 342-348.

Deamer, et al., "Characterization of nucleic acids by nanopore analysis", ACC Chem Res, 35(10), 2002, 817-825.

Deamer, et al., "Nanopores and nucleic acids: prospects for ultrarapid sequencing", Trends Biotechnol, 18(4), 2000, 147-151.

Doublie, et al., "Crystal structure of a bacteriophage T7 DNA replication complex at 2.2 A resolution", Nature, 391, 1998, 251-258.

Dressman, et al., "Transforming single DNA molecules into fluorescent magnetic particles for detection and enumeration of genetic variations", PNAS, 100(15), 2003, 8817-8822.

Eltoukhy, et al., "A 0.18um CMOS bioluminescence detection lab-on-chip", IEEE Journal of Solid-State Circuits Society 41(3):651-662, 2006.

Fedurco, et al., "BTA, a novel reagent for DNA attachment on glass and efficient generation of solid-phase amplified DNA colonies", Nucleic Acids Res. 34(3):e22, 2006.

Genomeweb Article, "PacBio Sys 'Strobe Sequencing' Increases Effective Read Length of Single-Molecular Sequencer", May 12, 2009.

Healy, "Nanopore-based single-molecule DNA analysis", Nanomed. 2(4), 2007, 459-481.

Korlach, et al., "Selective aluminum passivation for targeted immobilization of single DNA polymerase molecules in zero-mode waveguide nanostructures", PNAS, 105(4), 2008, 1176-1181.

Levene, et al., "Zero-Mode Waveguides for Single-Molecule Analysis at high concentrations", Science 299, 2003, 682-686.

Li, et al., "DNA molecules and configurations in a solid-state nanopore microscope", Nature Mater, 2(9), 2003, 611-615.

Lundquist, et al., "Parallel confocal detection of single molecules in real time", Opt. Lett. 33(9), 2008, 1026-1028.

Metzker, et al., "Emerging technologies in DNA sequencing", Genome Research, 15, 2005, 1767-1776.

Mitra, et al., "In situ localized amplification and contact replication of many individual DNA molecules", Nucleic Acids Research, Oxford University Press, GB vol. 27 No. 24, 1999, p. e34.

Prober, et al., "A System for Rapid DNA Sequencing with Fluorescent Chain-Terminating Dideoxynucleotides", Science, vol. 238, 1987, 336-341.

Raja, et al., "DNA Sequencing Using Differential Extension with Nucleotide Subsets (DENS)", Nucleic Acids Research 25(4), 1997, 800-805.

Ronaghi, et al., "A Sequencing Method Based on Real-Time Phyrphosphate", Science. Jul. 17, 1998; 281 (5375):363-365.

Ronaghi, et al., "Real-time DNA sequencing using detection of pyrophosphate release", Anal. Biochem. Nov. 1, 1996; 242 (1):84-89.

Ronaghi, "Pyrosequencing sheds light on DNA sequencing", Genome Res, 11(1), 2001, 3-11.

Ruparel, et al., "Design and synthesis of a 3'-O-allyl photocleavable fluorescent nucleotide as a reversible terminator for DNA sequencing by synthesis", PNAS, 102, 2005, 5932-5937.

Seo, et al., "Four-color DNA sequencing by synthesis on a chip using photocleavable fluorescent nucleotides", PNAS 102(17), 2005, 5926-5931.

Smith, et al., "Fluorescence detection in automated DNA sequence analysis", Nature, 321, 1986, 674-679.

Soni, "Progress toward Ultrafast DNA Sequencing Using Solid-State Nanopores", Clin CHem, 53(11), 2007, 1996-2001.

Zhu, et al., "Directly labeled DNA probes using fluorescent nucleotides with different length linkers", Nucleic Acids Research, 22(16), 1994, 3418-3422.

Maxam, et al., "A new method for sequencing DNA," Proceedings of the National Academy of Sciences, vol. 74, No. 2, Feb. 1, 1977, 560-564.

Mir, et al., "Sequencing by cyclic ligation and cleavage (CycLiC) directly on microarray captured template," Nucleic Acids Research, vol. 37, No. 1, Nov. 16, 2008, e5, 1-8.

\* cited by examiner

| Target sequence (SEQ ID NO: 01): | T | C | C | G | A | C | T | A | G | G | C | A |
|---|---|---|---|---|---|---|---|---|---|---|---|---|
| Doublet in delivery step: | A/C | G/T | | A/C | G/T | | A/C | G/T | A/C | | G/T | A/C |
| Signal intensity: | 1X | 2X | | 2X | 1X | | 1X | 2X | 2X | | 2X | 1X |
| 1st Predicted sequence (SEQ ID NO: 02): | G/T | A/C | A/C | G/T | A/C | A/C | G/T | A/C | G/T | G/T | A/C | A/C |

First Round of Doublet Sequencing: [A/C] and [G/T]

| Target sequence (SEQ ID NO: 01): | T | C | C | G | A | C | T | A | G | G | C | A |
|---|---|---|---|---|---|---|---|---|---|---|---|---|
| Doublet in delivery step: | | A/G | C/T | A/G | C/T | A/G | C/T | | C/T | A/G | A/G | A/G |
| Signal intensity: | | 3X | 2X | 2X | 1X | 3X | 2X | | 1X | 1X | | |
| 2nd Predicted sequence (SEQ ID NO: 03): | C/T | C/T | C/T | A/G | A/G | A/G | C/T | A/G | C/T | A/G | C/T | A/G |

Second Round of Doublet Sequencing: [A/G] and [C/T]

| 1st Predicted sequence (SEQ ID NO: 02): | G/T | A/C | A/C | G/T | A/C | A/C | G/T | A/C | G/T | G/T | A/C | A/C |
|---|---|---|---|---|---|---|---|---|---|---|---|---|
| 2nd Predicted sequence (SEQ ID NO: 03): | C/T | C/T | C/T | A/G | A/G | A/G | C/T | A/G | C/T | A/G | C/T | A/G |
| Combined sequence (SEQ ID NO: 01): | T | C | C | G | A | C | T | A | G | G | C | A |

Combined Predicted Sequences

FIG. 2

METHOD OF MAKING AN ARRAY OF NUCLEIC ACID COLONIES

REFERENCE TO RELATED APPLICATIONS

This is a continuation of non-provisional application U.S. Ser. No. 12/641,104, filed on Dec. 17, 2009, now U.S. Pat. No. 8,236,532, which claims priority to U.S. Provisional Application No. 61/140,566, filed on Dec. 23, 2008, each of which is incorporated herein by reference in its entirety.

REFERENCE TO SEQUENCE LISTING

The present application incorporates by reference the entirety of the Sequence Listing that was filed in computer readable form on Dec. 17, 2009, in connection with U.S. Ser. No. 12/641,104 filed on Dec. 17, 2009.

STATEMENT REGARDING FEDERALLY SPONSORED RESEARCH

This invention was made with Government support under NIH Grant R501HG003571-06 awarded by the PHS. The Government has certain rights in the invention.

FIELD OF THE INVENTION

The present technology relates to molecular sciences, such as genomics. More particularly, the present technology relates to nucleic acid sequencing.

BACKGROUND

The detection of specific nucleic acid sequences present in a biological sample has been used, for example, as a method for identifying and classifying microorganisms, diagnosing infectious diseases, detecting and characterizing genetic abnormalities, identifying genetic changes associated with cancer, studying genetic susceptibility to disease, and measuring response to various types of treatment. A common technique for detecting specific nucleic acid sequences in a biological sample is nucleic acid sequencing.

Nucleic acid sequencing methodology has evolved significantly from the chemical degradation methods used by Maxam and Gilbert and the strand elongation methods used by Sanger. Today several sequencing methodologies are in use which allow for the parallel processing of thousands of nucleic acids all in a single sequencing run. As such, the information generated from a single sequencing run can be enormous.

SUMMARY

The present technology relates to methods for obtaining nucleic acid sequence information. Such methods can permit long read lengths of target nucleic acids.

Some methods described herein include the steps of (a) providing a first sequencing reagent to a target nucleic acid in the presence of a polymerase, wherein the first sequencing reagent includes at least two different nucleotide monomers, and (b) providing a second sequencing reagent to the target nucleic acid, wherein the second sequencing reagent comprises one or more nucleotide monomers, at least one of the one or more nucleotide monomers being different from the nucleotide monomers present in the first sequencing reagent, and wherein the second sequencing reagent is provided subsequent to providing the first sequencing reagent, whereby sequence information for at least a portion of the target nucleic acid is obtained.

In some embodiments of the methods described herein, the at least two different nucleotide monomers of the first sequencing reagent are separately provided to the target nucleic acid.

In some embodiments of the methods described herein, the at least two different nucleotide monomers of the first sequencing reagent can be provided together to the target nucleic acid.

Other embodiments of the above-described methods, can further include repeating the method steps.

In some embodiments of the above-described methods, the polymerase extends a polynucleotide strand. Such embodiments can further include detecting the incorporation of at least one nucleotide monomer into the polynucleotide strand. In certain embodiments, the detecting can include detecting pyrophosphate. In particular embodiments, the detecting can include detecting a label.

In some embodiments of the above-described methods, the first sequencing reagent can include no more than two nucleotide monomers. In certain embodiments, the second sequencing reagent can include two different nucleotide monomers which are different from the two nucleotide monomers of the first sequencing reagent.

In some embodiments of the above-described methods, the first sequencing reagent can include no more than three nucleotide monomers. In certain embodiments, the second sequencing reagent can include one nucleotide monomer which is different from the nucleotide monomers of the first sequencing reagent.

In other embodiments of the methods described herein, the first sequencing reagent can include a nucleotide monomer comprising a label. In still other embodiments, the second sequencing reagent can include a nucleotide monomer comprising a label. In embodiments where labels are utilized, the label can be selected from the group consisting of fluorescent moieties, chromophores, antigens, dyes, phosphorescent groups, radioactive materials, chemiluminescent moieties, scattering or fluorescent nanoparticles, Raman signal generating moieties, and electrochemical detection moieties. Further embodiments can include cleaving the label from the nucleotide monomer.

In certain embodiments of the above-described methods, the first and/or second sequencing reagent can include a nucleotide monomer comprising a reversibly terminating moiety. In some of these embodiments, the terminating moiety can include a reversible terminating moiety.

In embodiments where nucleotide monomers include a reversible terminator, the method of obtaining sequence information can further include cleaving the reversible terminating moiety.

In some embodiments of the methods described herein, the first sequencing reagent and/or the second sequencing reagent include nucleotide monomers selected from the group consisting of deoxyribonucleotides, modified deoxyribonucleotides, ribonucleotides, modified ribonucleotides, peptide nucleotides, modified peptide nucleotides, modified phosphate sugar backbone nucleotides and mixtures thereof.

In some embodiments of the above-identified methods, the first sequencing reagent is provided to a single target nucleic acid. In other embodiments, the first sequencing reagent is provided simultaneously to a plurality of target nucleic acids. In such embodiments, the plurality of target nucleic acids can include target nucleic acids having different nucleotide sequences.

In certain embodiments of the methods described herein, the first sequencing reagent is provided to a plurality of target nucleic acids on a surface of an array in parallel. In such embodiments, the plurality of target nucleic acids can include target nucleic acids having the same or different nucleotide sequences.

In other embodiments, the polymerase utilized in the methods described herein includes a polymerase selected from the group consisting of a DNA polymerase, an RNA polymerase, a reverse transcriptase, and mixtures thereof. In still other embodiments, the polymerase can be a thermostable polymerase or a thermodegradable polymerase.

Additional methods for obtaining nucleic acid sequence information include the steps of (a) providing a first sequencing reagent to a target nucleic acid, wherein the first sequencing reagent comprises at least two different nucleotide monomers, (b) detecting the incorporation of a nucleotide monomer present in the first sequencing reagent into a polynucleotide strand complementary to at least a portion of the target nucleic acid, (c) providing a second sequencing reagent to said target nucleic acid, wherein the second sequencing reagent comprises one or more nucleotide monomers, at least one of the one or more nucleotide monomers being different from the nucleotide monomers present in the first sequencing reagent, and wherein the second sequencing reagent is provided subsequent to providing the first sequencing reagent, and (d) detecting the incorporation of a nucleotide monomer present in the second sequencing reagent into the polynucleotide strand, thereby obtaining sequence information for at least a portion of the target nucleic acid.

Other embodiments of the above-described methods, can further include repeating the method steps.

In some embodiments of the above-described methods, the at least two different nucleotide monomers of the first sequencing reagent are separately provided to the target nucleic acid.

In some embodiments of the above-described methods, the at least two different nucleotide monomers of the first sequencing reagent are provided together to the target nucleic acid.

In certain embodiments of the above-described methods, the detecting can include detecting pyrophosphate. In particular embodiments, the detecting can include detecting a label.

In some embodiments of the above-described methods, the first sequencing reagent can include no more than two nucleotide monomers. In certain embodiments, the second sequencing reagent can include two different nucleotide monomers, which are different from the two nucleotide monomers of the first sequencing reagent.

In some embodiments of the above-described methods, the first sequencing reagent includes no more than three nucleotide monomers. In certain embodiments, the second sequencing reagent can include one nucleotide monomer, which is different from the nucleotide monomers of the first sequencing reagent.

In other embodiments of the above-described methods, the first sequencing reagent can include a nucleotide monomer comprising a label. In still other embodiments, the second sequencing reagent can include a nucleotide monomer comprising a label. In embodiments where labels are utilized, the said label can be selected from the group consisting of fluorescent moieties, chromophores, antigens, dyes, phosphorescent groups, radioactive materials, chemiluminescent moieties, scattering or fluorescent nanoparticles, Raman signal generating moieties, and electrochemical detection moieties. Further embodiments can include cleaving the label from the nucleotide monomer.

In certain embodiments of the above-described methods, the first and/or second sequencing reagent can include a nucleotide monomer comprising a reversibly terminating moiety. In some of these embodiments, the terminating moiety can include a reversible terminating moiety.

In embodiments where nucleotide monomers include a reversible terminator, the method of obtaining sequence information can further include cleaving the reversible terminating moiety.

In some embodiments of the above-described methods, the first sequencing reagent and/or the second sequencing reagent can include nucleotide monomers selected from the group consisting of deoxyribonucleotides, modified deoxyribonucleotides, ribonucleotides, modified ribonucleotides, peptide nucleotides, modified peptide nucleotides, modified phosphate sugar backbone nucleotides and mixtures thereof.

In some embodiments of the above-identified methods, the first sequencing reagent is provided to a single target nucleic acid. In other embodiments, the first sequencing reagent is provided simultaneously to a plurality of target nucleic acids. In such embodiments, the plurality of target nucleic acids can include target nucleic acids having different nucleotide sequences.

In certain embodiments of the methods described herein, the first sequencing reagent is provided to a plurality of target nucleic acids on a surface of an array in parallel. In such embodiments, the plurality of target nucleic acids can include target nucleic acids having the same or different nucleotide sequences.

Additional methods for obtaining nucleic acid sequence information can include the steps of (a) providing a first sequencing reagent to a target nucleic acid in the presence of a polymerase, wherein the first sequencing reagent comprises at least two different nucleotide monomers, (b) removing at least a portion of the first sequencing reagent, and (c) providing a second sequencing reagent to the target nucleic acid, wherein the second sequencing reagent comprises one or more nucleotide monomers, at least one of the one or more nucleotide monomers being different from the nucleotide monomers present in the first sequencing reagent, whereby sequence information for at least a portion of the target nucleic acid is obtained.

In some embodiments of the above-described methods, the at least two different nucleotide monomers of the first sequencing reagent can be separately provided to the target nucleic acid.

In some embodiments of the methods described herein, the at least two different nucleotide monomers of the first sequencing reagent can be provided together to the target nucleic acid.

Other embodiments of the above-described methods, can further include repeating the method steps.

In some embodiments of the above-described methods, the polymerase extends a polynucleotide strand. Such embodiments can further include detecting the incorporation of at least one nucleotide monomer into the polynucleotide strand. In certain embodiments, the detecting can include detecting pyrophosphate. In particular embodiments, the detecting can include detecting a label.

In some embodiments of the above-described methods, the first sequencing reagent can include no more than two nucleotide monomers. In certain embodiments, the second sequencing reagent can include two different nucleotide monomers which are different from the two nucleotide monomers of the first sequencing reagent.

In some embodiments of the above-described methods, the first sequencing reagent can include no more than three nucleotide monomers. In certain embodiments, the second sequencing reagent can include one nucleotide monomer which is different from the nucleotide monomers of the first sequencing reagent.

In other embodiments of the methods described herein, the first sequencing reagent can include a nucleotide monomer comprising a label. In still other embodiments, the second sequencing reagent can include a nucleotide monomer comprising a label. In embodiments where labels are utilized, the label can be selected from the group consisting of fluorescent moieties, chromophores, antigens, dyes, phosphorescent groups, radioactive materials, chemiluminescent moieties, scattering or fluorescent nanoparticles, Raman signal generating moieties, and electrochemical detection moieties. Further embodiments can include cleaving the label from the nucleotide monomer.

In certain embodiments of the above-described methods, the first and/or second sequencing reagent can include a nucleotide monomer comprising a reversibly terminating moiety. In some of these embodiments, the terminating moiety can include a reversible terminating moiety.

In embodiments where nucleotide monomers include a reversible terminator, the method of obtaining sequence information can further include cleaving the reversible terminating moiety.

In some embodiments of the methods described herein, the first sequencing reagent and/or the second sequencing reagent include nucleotide monomers selected from the group consisting of deoxyribonucleotides, modified deoxyribonucleotides, ribonucleotides, modified ribonucleotides, peptide nucleotides, modified peptide nucleotides, modified phosphate sugar backbone nucleotides and mixtures thereof.

In some embodiments of the above-described methods, the first sequencing reagent is provided to a single target nucleic acid. In other embodiments, the first sequencing reagent can be provided simultaneously to a plurality of target nucleic acids. In such embodiments, the plurality of target nucleic acids can include target nucleic acids having different nucleotide sequences.

In certain embodiments of the above-described methods, the first sequencing reagent can be provided to a plurality of target nucleic acids on a surface of an array in parallel. In such embodiments, the plurality of target nucleic acids can include target nucleic acids having the same or different nucleotide sequences.

In other embodiments, the polymerase utilized in the above-described methods can include a polymerase selected from the group consisting of a DNA polymerase, an RNA polymerase, a reverse transcriptase, and mixtures thereof. In still other embodiments, the polymerase can be a thermostable polymerase or a thermodegradable polymerase.

Additional methods of obtaining nucleic acid sequence information can include the steps of (a) providing a first sequencing reagent to a target nucleic acid in the presence of a polymerase, wherein the first sequencing reagent comprises at least two different nucleotide monomers, and wherein the polymerase incorporates at least one nucleotide monomer of the first sequencing reagent into a polynucleotide strand, thereby producing pyrophosphate, (b) removing at least a portion of the pyrophosphate, and (c) providing a second sequencing reagent to the target nucleic acid, wherein the second sequencing reagent comprises one or more nucleotide monomers, at least one of the one or more nucleotide monomers being different from the nucleotide monomers present in the first sequencing reagent, whereby sequence information for at least a portion of the target nucleic acid is obtained.

In some embodiments of the methods described herein, the at least two different nucleotide monomers of the first sequencing reagent are separately provided to the target nucleic acid.

In some embodiments of the methods described herein, the at least two different nucleotide monomers of the first sequencing reagent can be provided together to the target nucleic acid.

Other embodiments of the methods described herein can further include repeating the method steps.

In some embodiments of the methods described herein, the polymerase can extend a polynucleotide strand. Such methods can further include detecting the incorporation of at least one nucleotide monomer into the polynucleotide strand. In certain embodiments, the detecting can include detecting pyrophosphate.

In some embodiments of the above-described methods, the first sequencing reagent can include no more than two nucleotide monomers. In certain embodiments, the second sequencing reagent can include two different nucleotide monomers which are different from the two nucleotide monomers of the first sequencing reagent.

In some embodiments of the above-described methods, the first sequencing reagent can include no more than three nucleotide monomers. In certain embodiments, the second sequencing reagent can include one nucleotide monomer which is different from the nucleotide monomers of the first sequencing reagent.

In some embodiments of the above-described methods, the first sequencing reagent and/or the second sequencing reagent can include nucleotide monomers selected from the group consisting of deoxyribonucleotides, modified deoxyribonucleotides, ribonucleotides, modified ribonucleotides, peptide nucleotides, modified peptide nucleotides, modified phosphate sugar backbone nucleotides and mixtures thereof.

In some embodiments of the above-identified methods, the first sequencing reagent is provided to a single target nucleic acid. In other embodiments, the first sequencing reagent is provided simultaneously to a plurality of target nucleic acids. In such embodiments, the plurality of target nucleic acids can include target nucleic acids having different nucleotide sequences.

In certain embodiments of the methods described herein, the first sequencing reagent is provided to a plurality of target nucleic acids on a surface of an array in parallel. In such embodiments, the plurality of target nucleic acids can include target nucleic acids having the same or different nucleotide sequences.

In other embodiments, the polymerase utilized in the methods described herein includes a polymerase selected from the group consisting of a DNA polymerase, an RNA polymerase, a reverse transcriptase, and mixtures thereof. In still other embodiments, the polymerase can be a thermostable polymerase or a thermodegradable polymerase.

Even more methods for obtaining nucleic acid sequence information can include the steps of (a) detecting the incorporation of a nucleotide monomer present in a first sequencing reagent into a polynucleotide strand complementary to at least a portion of a target nucleic acid, wherein the first sequencing reagent comprises at least two different nucleotide monomers, (b) removing at least a portion of the first sequencing reagent, and (c) detecting the incorporation of a nucleotide monomer present in a second sequencing reagent into the polynucleotide strand, wherein the second sequencing reagent comprises one or more nucleotide monomers, at least one of the one or more nucleotide monomers being different from the nucleotide monomers present in the first sequencing reagent, whereby sequence information for at least a portion of the target nucleic acid is obtained.

Other embodiments of the above-described methods, can further include repeating the method steps.

In some embodiments of the above-described methods, the detecting can include detecting pyrophosphate. In particular embodiments, the detecting can include detecting a label.

In some embodiments of the above-described methods, the first sequencing reagent can include no more than two nucleotide monomers. In certain embodiments, the second sequencing reagent can include two different nucleotide monomers, which are different from the two nucleotide monomers of the first sequencing reagent.

In some embodiments of the above-described methods, the first sequencing reagent includes no more than three nucleotide monomers. In certain embodiments, the second sequencing reagent can include one nucleotide monomer, which is different from the nucleotide monomers of the first sequencing reagent.

In other embodiments of the above-described methods, the first sequencing reagent can include a nucleotide monomer comprising a label. In still other embodiments, the second sequencing reagent can include a nucleotide monomer comprising a label. In embodiments where labels are utilized, the said label can be selected from the group consisting of fluorescent moieties, chromophores, antigens, dyes, phosphorescent groups, radioactive materials, chemiluminescent moieties, scattering or fluorescent nanoparticles, Raman signal generating moieties, and electrochemical detection moieties. Further embodiments can include cleaving the label from the nucleotide monomer.

In certain embodiments of the above-described methods, the first and/or second sequencing reagent can include a nucleotide monomer comprising a reversibly terminating moiety. In some of these embodiments, the terminating moiety can include a reversible terminating moiety.

In embodiments where nucleotide monomers include a reversible terminator, the method of obtaining sequence information can further include cleaving the reversible terminating moiety.

In some embodiments of the above-described methods, the first sequencing reagent and/or the second sequencing reagent can include nucleotide monomers selected from the group consisting of deoxyribonucleotides, modified deoxyribonucleotides, ribonucleotides, modified ribonucleotides, peptide nucleotides, modified peptide nucleotides, modified phosphate sugar backbone nucleotides and mixtures thereof.

In some embodiments of the above-identified methods, the first sequencing reagent is provided to a single target nucleic acid. In other embodiments, the first sequencing reagent is provided simultaneously to a plurality of target nucleic acids. In such embodiments, the plurality of target nucleic acids can include target nucleic acids having different nucleotide sequences.

In certain embodiments of the methods described herein, the first sequencing reagent is provided to a plurality of target nucleic acids on a surface of an array in parallel. In such embodiments, the plurality of target nucleic acids can include target nucleic acids having the same or different nucleotide sequences.

Some methods for obtaining nucleic acid sequence information described herein can include the steps of (a) detecting pyrophosphate release by the incorporation of a nucleotide monomer present in a first sequencing reagent into a polynucleotide strand complementary to at least a portion of a target nucleic acid, wherein the first sequencing reagent comprises at least two different nucleotide monomers, (b) removing at least a portion of the pyrophosphate, and (c) detecting the incorporation of a nucleotide monomer present in a second sequencing reagent into the polynucleotide strand complementary to at least a portion of a target nucleic acid, wherein the second sequencing reagent comprises one or more nucleotide monomers, at least one of the one or more nucleotide monomers being different from the nucleotide monomers present in the first sequencing reagent, whereby sequence information for at least a portion of the target nucleic acid is obtained.

Other embodiments of the above-described methods, can further include repeating the method steps.

In some embodiments of the above-described methods, the first sequencing reagent can include no more than two nucleotide monomers. In certain embodiments, the second sequencing reagent can include two different nucleotide monomers, which are different from the two nucleotide monomers of the first sequencing reagent.

In some embodiments of the above-described methods, the first sequencing reagent includes no more than three nucleotide monomers. In certain embodiments, the second sequencing reagent can include one nucleotide monomer, which is different from the nucleotide monomers of the first sequencing reagent.

In some embodiments of the above-described methods, the first sequencing reagent and/or the second sequencing reagent can include nucleotide monomers selected from the group consisting of deoxyribonucleotides, modified deoxyribonucleotides, ribonucleotides, modified ribonucleotides, peptide nucleotides, modified peptide nucleotides, modified phosphate sugar backbone nucleotides and mixtures thereof.

In some embodiments of the above-identified methods, the first sequencing reagent is provided to a single target nucleic acid. In other embodiments, the first sequencing reagent is provided simultaneously to a plurality of target nucleic acids. In such embodiments, the plurality of target nucleic acids can include target nucleic acids having different nucleotide sequences.

In certain embodiments of the methods described herein, the first sequencing reagent is provided to a plurality of target nucleic acids on a surface of an array in parallel. In such embodiments, the plurality of target nucleic acids can include target nucleic acids having the same or different nucleotide sequences.

Some methods for obtaining nucleic acid sequence information described herein can include the steps of (a) detecting the incorporation of a nucleotide monomer present in a first sequencing reagent into a first polynucleotide strand complementary to at least a portion of a target nucleic acid, wherein the first sequencing reagent comprises at least two different nucleotide monomers, (b) detecting the incorporation of a nucleotide monomer present in a second sequencing reagent into the first polynucleotide strand, wherein the second sequencing reagent comprises one or more nucleotide monomers, at least one of the one or more nucleotide monomers being different from the nucleotide monomers present in the first sequencing reagent, (c) removing the first polynucleotide strand, and (d) detecting the incorporation of a nucleotide monomer present in a third sequencing reagent into a second polynucleotide strand complementary to at least a portion of the target nucleic acid, wherein the third sequencing reagent comprises two or more nucleotide monomers, wherein at least one of the two or more nucleotide monomers is different from the at least two different nucleotide monomers present in the first sequencing reagent.

In some embodiments of the above-identified methods, the first sequencing reagent can include no more than two nucleotide monomers. In certain embodiments, the second sequencing reagent can include two different nucleotide monomers which are different from the two nucleotide monomers of the first sequencing reagent. In further embodiments, the third sequencing reagent can include two nucleotide monomers, wherein at least one of the two nucleotide monomers is different from the at least two nucleotide monomers present in the first sequencing reagent.

In some embodiments of the above-identified methods, the first sequencing reagent can include no more than three nucleotide monomers. In certain embodiments, the second sequencing reagent can include one nucleotide monomer which is different from the nucleotide monomers of the first sequencing reagent. In further embodiments, the third sequencing reagent can include three nucleotide monomers, wherein one of the three nucleotide monomers is different from the at least two nucleotide monomers.

In some embodiments of the above-identified methods, the first sequencing reagent can include a nucleotide monomer comprising a label. In still other embodiments, the second sequencing reagent can include a nucleotide monomer comprising a label. In yet other embodiments, the third sequencing reagent can include a nucleotide monomer comprising a label. In embodiments where labels are utilized, the label can be selected from the group consisting of fluorescent moieties, chromophores, antigens, dyes, phosphorescent groups, radioactive materials, chemiluminescent moieties, scattering or fluorescent nanoparticles, Raman signal generating moieties, and electrochemical detection moieties. Further embodiments can include cleaving the label from the nucleotide monomer.

In certain embodiments of the above-described methods, the first and/or second sequencing reagent can include a nucleotide monomer comprising a reversibly terminating moiety. In some of these embodiments, the terminating moiety can include a reversible terminating moiety.

In embodiments where nucleotide monomers include a reversible terminator, the method of obtaining sequence information can further include cleaving the reversible terminating moiety.

In some embodiments of the above-identified methods, the first sequencing reagent, the second sequencing reagent and/ or the third sequencing reagent can include nucleotide monomers selected from the group consisting of deoxyribonucleotides, modified deoxyribonucleotides, ribonucleotides, modified ribonucleotides, peptide nucleotides, modified peptide nucleotides, modified phosphate sugar backbone nucleotides and mixtures thereof.

In some embodiments of the above-identified methods, the first sequencing reagent is provided to a single target nucleic acid. In other embodiments, the first sequencing reagent is provided simultaneously to a plurality of target nucleic acids. In such embodiments, the plurality of target nucleic acids can include target nucleic acids having different nucleotide sequences.

In certain embodiments of the methods described herein, the first sequencing reagent is provided to a plurality of target nucleic acids on a surface of an array in parallel. In such embodiments, the plurality of target nucleic acids can include target nucleic acids having the same or different nucleotide sequences.

Additional methods for obtaining nucleic acid sequence information can include the steps of (a) providing a first low resolution sequence representation for a target nucleic acid, wherein the first low resolution sequence representation is degenerate with respect to two or more nucleotide types, (b) providing a second low resolution sequence representation for the target nucleic acid, wherein the second low resolution sequence representation is degenerate with respect to two or more nucleotide types, wherein at least one of the two or more nucleotide types in the first low resolution sequence representation is different from at least one of the two or more nucleotide types in the second low resolution sequence representation, and (c) comparing the first low resolution sequence representation and the second low resolution sequence representation to determine the actual sequence of the target nucleic acid at single nucleotide resolution.

In some embodiments of the above-described methods, the method can be carried out by a computer. For example, the low resolution sequence representations can be provided to a computer that is programmed to compare the representations to determine the actual sequence of the target nucleic acid at single nucleotide resolution. The computer can be further programmed to store one or more of the representations and the actual sequence. The computer can be programmed to transmit one or more of the representations and the actual sequence to a user, to another computer or to a network.

In particular embodiments of the above-described methods, the first low resolution sequence representation can be degenerate with respect to a pair of nucleotide types.

In certain embodiments, the first low resolution sequence representation can be degenerate with respect to two pairs of nucleotide types. For example, the first low resolution sequence representation can be degenerate with respect to A and T at particular positions in the actual sequence of the target nucleic acid and the first low resolution sequence representation can be degenerate with respect to G and C at particular positions in the actual sequence of the target nucleic acid. Continuing with the example, the second low resolution sequence representation can be degenerate with respect to A and C at particular positions in the actual sequence of the target nucleic acid and the second low resolution sequence representation can be degenerate with respect to G and T at particular positions in the actual sequence of the target nucleic acid. Alternatively, the second low resolution sequence representation can be degenerate with respect to A and G at particular positions in the actual sequence of the target nucleic acid and the second low resolution sequence representation can be degenerate with respect to C and T at particular positions in the actual sequence of the target nucleic acid.

In some embodiments of the above-described methods, the first low resolution sequence representation can be degenerate with respect to a triplet of nucleotide types.

In particular embodiments of the above-described methods, the first low resolution sequence representation can include a string of symbols and the number of different symbol types in the string can be less than the number of different nucleotide types in the actual sequence of the nucleic acid.

One or more low resolution sequence representations used in a method set forth above can be obtained from a sequencing reaction that includes the repeated steps of (i) detecting the incorporation of a first sequencing reagent into a polynucleotide strand complementary to at least a portion of the target nucleic acid, wherein said first sequencing reagent comprises at least two different nucleotide monomers, and (ii) detecting the incorporation of a second sequencing reagent into the polynucleotide strand, wherein said second sequencing reagent comprises one or more nucleotide monomers, at least one of said one or more nucleotide monomers being different from the nucleotide monomers present in said first sequencing reagent.

In particular embodiments of the methods set forth above, pattern recognition methods can be used to determine the actual sequence of a target nucleic acid at single nucleotide resolution.

A comparing step of a method set forth above, can be carried out by alignment of the first low resolution sequence representation and the second low resolution sequence to reference sequences in a database, wherein the reference sequences include the actual sequence of the target nucleic acid.

Also provided are methods for determining the presence or absence of a target nucleic acid. Such methods can include the steps of (a) providing a first low resolution sequence representation for a target nucleic acid, wherein the target nucleic acid is obtained from a target sample, wherein the first low resolution sequence representation is degenerate with respect to two or more nucleotide types, (b) providing a second low resolution sequence representation for the target nucleic acid, wherein the target nucleic acid is obtained from a reference sample, wherein the second low resolution sequence representation is degenerate with respect to two or more nucleotide types, and (c) comparing the first low resolution sequence representation and the second low resolution sequence representation to determine the presence or absence of the target nucleic acid in the target sample.

In particular embodiments of the above-described methods, the two or more nucleotide types in the first low resolution sequence representation are the same as the two or more nucleotide types in the second low resolution sequence representation, In some embodiments of the above-described methods, a first plurality of low resolution sequence representations for a plurality of nucleic acids in the target sample are provided and a second plurality of low resolution sequence representations for a plurality of nucleic acids in the reference sample are provided. Furthermore, the first low resolution sequence representation for the target nucleic acid and the second low resolution sequence representation for the target nucleic acid can be distinguished from low resolution sequence representations in the first plurality and in the second plurality.

Embodiments of the above-described methods can further include quantifying the amount of the target nucleic acid in the target sample relative to the amount of the target nucleic acid in the reference sample. For example, the target nucleic acid can be an mRNA and the amount can be indicative of an expression level for the mRNA.

In particular embodiments of the above-described methods, the first and second low resolution sequence representations have a known correlation with the actual sequence of the target nucleic acid at single nucleotide resolution.

In some embodiments of the above-described methods, the first low resolution sequence representation and the second low resolution sequence representation are the same.

BRIEF DESCRIPTION OF THE DRAWINGS

FIG. 2 is a diagram showing a doublet delivery and sequence determination scheme. In a first round of doublet sequencing on a target sequence (SEQ ID NO: 01), a $1^{st}$ predicted sequence (SEQ ID NO: 02) can be obtained. In a second round of doublet sequencing on the target sequence (SEQ ID NO: 01), a $2^{nd}$ predicted sequence (SEQ ID NO: 03) can be obtained. The $1^{st}$ and $2^{nd}$ predicted sequences can be combined to show the sequence of the target sequence (SEQ ID NO: 01).

DETAILED DESCRIPTION

Figure 1:
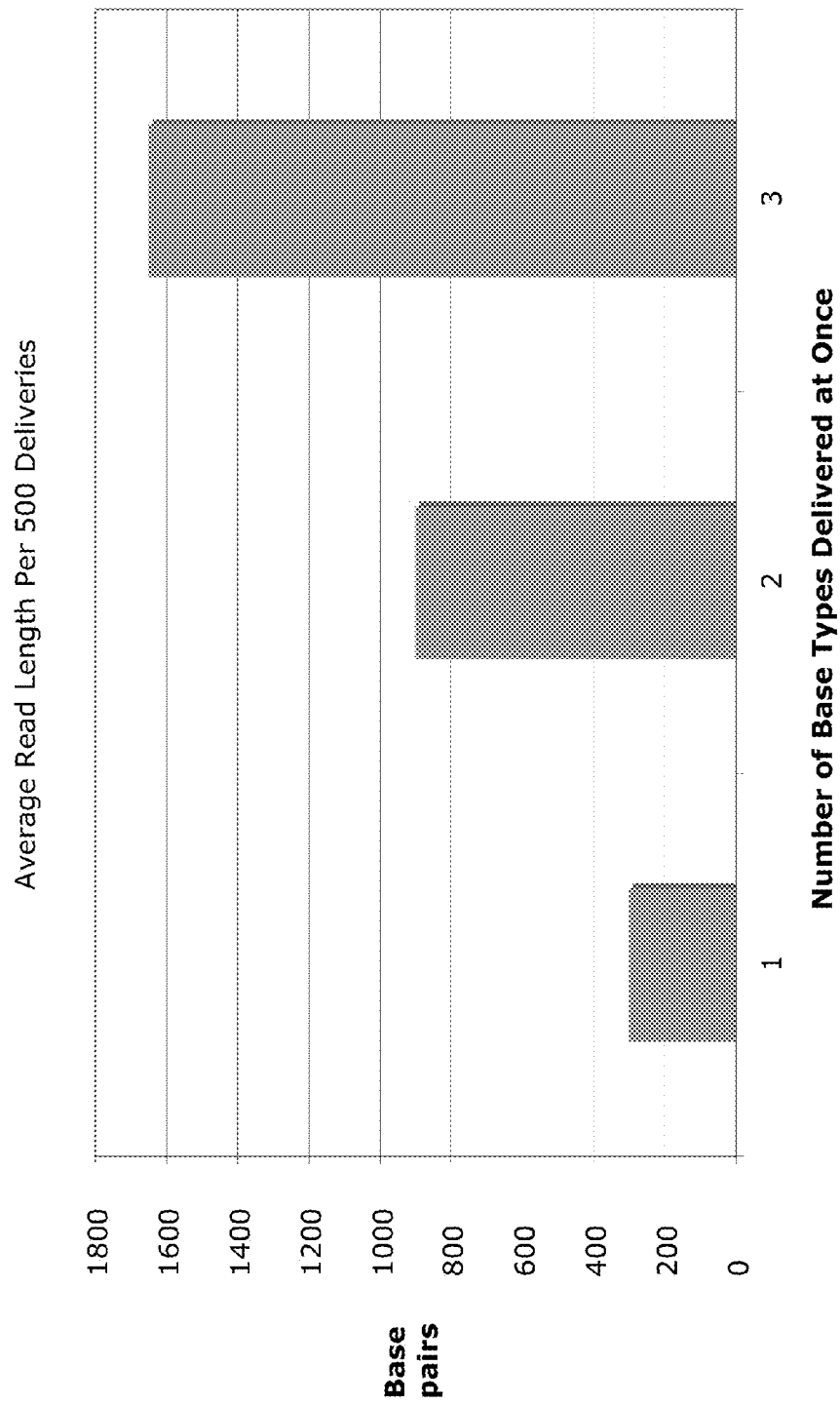
FIG. 1 is a graph depicting the length of base pair reads for single, doublet, and triplet delivery methods.

The present technology relates to methods for sequencing polymers such as nucleic acids. Some embodiments relate to sequencing-by-synthesis (SBS) methodologies. Particular embodiments relate to extending the read length produced by SBS and other sequencing methods.

Generally, SBS techniques include the enzymatic extension of a nascent polynucleotide strand complementary to a target nucleic acid template through the iterative addition of nucleotide monomers and determining the sequence of the target nucleic acid template based on the order of addition for the nucleotide monomers. In some SBS methods, each nucleotide monomer addition to a nascent polynucleotide can occur in a delivery step. Distinct delivery steps are repeated for each nucleotide, for example, dATP, dCTP, dGTP, and dTTP in a round of sequencing. In such SBS chemistries, the total number of deliveries can determine, in part, the upper limit of a particular read length in a sequencing run. However, without wishing to be bound to any theory, it is believed that particular non idealities, for example, properties of the nucleic acids being sequenced, such as presence of homopolymer sequence stretches; or manipulations involved in SBS chemistry, such as photooxidation of nucleic acids and other reagents due to irradiation with light; or chemical degradation due to contaminants in reagents, can result in significantly shorter read lengths than anticipated. In some instances, an average read length may be less than 60% of the number of nucleotide deliveries. Although the invention is exemplified herein using SBS methods of nucleic acid sequencing, the principles can be extended to other sequencing methods whether applied to nucleic acids or other polymers.

DEFINITIONS

As used herein, "a sequencing reagent" and grammatical equivalents thereof can refer to a composition, such as a solution, comprising one or more monomeric precursors of a polymer such as nucleotide monomers. In some embodiments, a sequencing reagent includes one or more nucleotide monomers having a label moiety, a terminator moiety, or both. Such moieties are chemical groups that are not naturally occurring moieties of nucleic acids, being introduced by synthetic means to alter the natural characteristics of the nucleotide monomers with regard to detectability under particular conditions or enzymatic reactivity under particular conditions. Alternatively, a sequencing reagent comprises one or more nucleotide monomers that lack a label moiety and/or a terminator moiety. In some embodiments, the sequencing reagent consists of or essentially consists of one nucleotide monomer, two different nucleotide monomers, three different nucleotide monomers or four different nucleotide monomers. It should be understood that when providing a sequencing reagent comprising multiple nucleotide monomers to a target nucleic acid, the nucleotide monomers do not necessarily have to be provided at the same time. However, in preferred embodiments of the methods described herein, multiple nucleotide monomers are provided together (at the same time) to the target nucleic acid. Irrespective of whether the multiple nucleotide monomers are provided to the target nucleic acid separately or together, the result is that the sequencing reagent, including the nucleotide monomers contained therein, are simultaneously in the presence of the target nucleic acid. For example, two nucleotide monomers can be delivered, either together or separately, to a target nucleic acid. In such embodiments, a sequencing reagent comprising two nucleotide monomers will have been provided to the target nucleic acid. In some embodiments, zero, one or two of the nucleotide monomers will be incorporated into a polynucleotide that is complementary to the target nucleic acid.

As used here, "complementary polynucleotides" includes polynucleotide strands that are not necessarily complementary to the full length of the target sequence. That is, a complementary polynucleotide can be complementary to only a portion of the target nucleic acid. As more nucleotide monomers are incorporated into the complementary polynucleotide, the complementary polynucleotide becomes complementary to a greater portion of the target nucleic acid. Typically, the complementary portion is a contiguous portion of the target nucleic acid.

As used herein, "a round of sequencing" or "a sequencing run" and/or grammatical variants thereof can refer to a repetitive process of physical or chemical steps that is carried out to obtain signals indicative of the order of monomers in a polymer. For example, the steps can be initiated on a nucleic acid target and carried out to obtain signals indicative of the order of bases in the nucleic acid target. The process can be carried out to its typical completion, which is usually defined by the point at which signals from the process can no longer distinguish bases of the target with a reasonable level of certainty. If desired, completion can occur earlier, for example, once a desired amount of sequence information has been obtained. A sequencing run can be carried out on a single target nucleic acid molecule or simultaneously on a population of target nucleic acid molecules having the same sequence, or simultaneously on a population of target nucleic acids having different sequences. In some embodiments, a sequencing run is terminated when signals are no longer obtained from one or more target nucleic acid molecules from which signal acquisition was initiated. For example, a sequencing run can be initiated for one or more target nucleic acid molecules that are present on a solid phase substrate and terminated upon removal of the one or more target nucleic acid molecules from the substrate or otherwise ceasing detection of the target nucleic acids that were present on the substrate when the sequencing run was initiated.

As used herein, "cycle" and/or grammatical variants thereof can refer to the portion of a sequencing run that is repeated to indicate the presence of at least one monomer in a polymer. Typically, a cycle includes several steps such as steps for delivery of reagents, washing away unreacted reagents and detection of signals indicative of changes occurring in response to added reagents. For example, a cycle of an SBS reaction can include delivery of a sequencing reagent that includes one or more type of nucleotide, washing to remove unreacted nucleotides, and detection to detect one or more nucleotides that are incorporated in an extended nucleic acid.

As used herein, "flow step" and/or "delivery" and grammatical equivalents thereof can refer to providing a sequencing reagent to a target polymer such as a target nucleic acid. In some embodiments, the sequencing reagent contains one or more nucleotide monomers. Flow steps or deliveries can be repeated in multiple cycles in a round of sequencing.

As used herein, "nucleotide monomer" and grammatical equivalents thereof can refer to a nucleotide or nucleotide analog that can become incorporated into a polynucleotide. In the methods described herein, the nucleotide monomers are separate non-linked nucleotides. That is, the nucleotide monomers are not present as dimers, trimers, etc. Such nucleotide monomers may be substrates for an enzyme that may extend a polynucleotide strand. Nucleotide monomers may or may not become incorporated into a nascent polynucleotide in a flow step. Examples of nucleotide monomers include deoxyribonucleotides, modified deoxyribonucleotides, ribonucleotides, modified ribonucleotides, peptide nucleotides, modified peptide nucleotides, modified phosphate sugar backbone nucleotides and mixtures thereof. Nucleotide analogs which include a modified nucleobase can also be used in the methods described herein. As is known in the art, certain nucleotide analogues cannot become incorporated into a polynucleotide, for example, nucleotide analogues such as adenosine 5' phosphosulfate.

Aspects of the methods described herein can include removing at least a portion of a substance from a site of activity. Such sites of activity can include sites of incorporation and/or detection. For example, a substance may be removed from the site of incorporation or the presence of a polymerase. Methods of removing a substance from a site of activity can include for example, washing the substance from the site, sequestering the substance from the site of activity, and degrading the substance.

As used herein, "a portion" and "at least a portion" and grammatical equivalents thereof can refer to any fraction of a whole amount. In some embodiments, "at least a portion" refers to at least about 10%, 20%, 30%, 40%, 50%, 60%, 70%, 80%, 90% and 100% of a whole amount.

As used herein, "sequence representation" and grammatical equivalents thereof, when used in reference to a polymer, can refer to information that signifies the order and type of monomeric units in the polymer. For example, the information can indicate the order and type of nucleotides in a nucleic acid. The information can be in any of a variety of formats including, for example, a depiction, image, electronic medium, series of symbols, series of numbers, series of letters, series of colors, etc. The information can be at single monomer resolution or at lower resolution, as set forth in further detail below. An exemplary polymer is a nucleic acid, such as DNA or RNA, having nucleotide units. A series of "A," "T," "G," and "C" letters is a well known sequence representation for DNA that can be correlated, at single nucleotide resolution, with the actual sequence of a DNA molecule. Other exemplary polymers are proteins having amino acid units and polysaccharides having saccharide units.

As used herein, "low resolution" and grammatical equivalents thereof, when used in reference to a sequence representation, can refer to a resolution at which at least a one type of monomeric unit in a polymer can be distinguished from at least a first other type of monomeric unit in the polymer, but cannot necessarily be distinguished from a second other type of monomeric unit in the polymer. For example, low resolution when used in reference to a sequence representation of a nucleic acid means that two or three of four possible nucleotide types can be indicated as candidate residents at a particular position in the sequence while the two or three nucleotide types cannot necessarily being distinguished from each other in the sequence representation. In particular embodiments, two different monomeric units from an actual polymer sequence can be assigned a common label or identifier in a low resolution sequence representation. In some embodiments, three different monomeric units from an actual polymer sequence can be assigned a common label or identifier in a low resolution sequence representation. Typically, the diversity of different characters in a low resolution sequence representation will be fewer than the diversity of different types of monomers in the polymer represented by the low resolution sequence representation. For example, a low resolution representation of a nucleic acid can include a string of symbols and the number of different symbol types in the string can be less than the number of different nucleotide types in the actual sequence of the nucleic acid.

As used herein "position" and grammatical equivalents thereof, when used in reference to a sequence, can refer to the location of a unit in the sequence. The location can be identified, for example, relative to other locations in the same sequence. Alternatively or additionally, the location can be identified with reference to another sequence or series. Although one or more characteristic of the unit may be known, any such characteristics need not be considered in identifying position.

As used herein, "degenerate" and grammatical equivalents thereof can refer to having more than one state or identification. When used in reference to a nucleic acid representation, the term refers to a position in the nucleic acid representation for which two or more nucleotide types are identified as candidate occupants in the corresponding position of the actual nucleic acid sequence. A degenerate position in a nucleic acid can have, for example, 2, 3 or 4 nucleotide types as candidate occupants. In particular embodiments, the number of different nucleotide types at a degenerate position in a sequence representation can be greater than one and less than three (i.e. two). In other embodiments, the number of different nucleotide types at a degenerate position in a sequence representation can be greater than one and less than four (i.e. two or three). Typically, the number of different nucleotide types at a degenerate position in a sequence representation can be less than the number of different nucleotide types present in the actual nucleic acid sequence that is represented.

Aspects of the current disclosure describe methods for extending the length of nucleic acid sequence reads obtained by sequencing methodologies. In some methods described herein, a sequencing reagent can be provided to a target nucleic acid in a single delivery in which the sequencing reagent comprises two or more different nucleotide monomers. At each delivery, two or more types of nucleotide monomer can be incorporated into a polynucleotide. Using such methods, long read lengths can be achieved because for any given cycle the polynucleotide can be extended by multiple nucleotides, whereas single nucleotide delivery methods might only yield multiple incorporations for regions of a template that are homopolymeric. Although a single sequencing run using only multiple nucleotide monomer delivery would typically provide a lower resolution than methods where one type of nucleotide monomer is provided at each delivery, resolutions at least on par with single nucleotide monomer delivery can be achieved by performing a second sequencing run using a doublet combination different from the doublet combination used in the first run. The difference between runs performed using multiple nucleotide monomer delivery as compared to single nucleotide delivery, however, is that the read length of the sequence obtained by multiple nucleotide monomer delivery can be significantly longer than the read length of a the sequence obtained by single nucleotide monomer delivery. Furthermore, as discussed in detail herein, there are several applications for lower resolution sequence obtained by single runs using multiple nucleotide monomer delivery.

In an exemplary embodiment, a doublet delivery method can be used. In such an embodiment, a sequencing reagent comprising two types of nucleotide monomer, for example, dATP and dCTP, can be provided in a first delivery to a target nucleic acid in the presence of polymerase. In the subsequent delivery, a sequencing reagent comprising two types of nucleotide monomers different from the nucleotide monomers of the previous delivery, for example, dGTP and dTTP can be provided to the target nucleic acid. The deliveries can be repeated and sequence information of the target nucleic acid can be obtained. In some embodiments, doublet delivery methods can provide sequence read lengths of at least 1.8 times the number of total deliveries (FIG. 1). This is in contrast to methods where single nucleotide monomers are provided in each delivery. In such methods, the typical read length is substantially less than the number of deliveries (FIG. 1).

In some doublet delivery methods, there can be three doublet delivery combinations that can be used, for example, dATP/dCTP+dGTP/dTTP; dATP/dGTP+dCTP/dTTP; and dATP/dTTP+dCTP/dGTP ([First delivery nucleotide monomers]+[Second delivery nucleotide monomers]).

It is contemplated that in some embodiments, a target nucleic acid may undergo at least two rounds of sequencing. For example, a first round may use one doublet delivery combination, and a second round may use a different doublet delivery combination. On combining the sequence data obtained from each round of sequencing, such embodiments can provide sequence information of a target nucleic acid at single-base resolution (Example 2, and FIG. 2).

Doublet delivery methods are also contemplated where a target nucleic acid can undergo three rounds of sequencing in which each doublet delivery combination is used. On combining the sequence data obtained from each round of sequencing, sequence information of the target nucleic acid can be obtained at single-base resolution with additional error checking.

In addition to doublet delivery methods, triplet delivery methods are also contemplated. Using such methods, a round of sequencing can be performed in which three different nucleotide monomers can be provided to a target nucleic acid in a delivery. In the next delivery, a nucleotide monomer which is different from the three nucleotide monomers of the previous delivery can be provided to the target nucleic acid. The combination of deliveries can be repeated for a round of sequencing and sequence information of the target nucleic acid can be obtained. In some embodiments, read lengths of at least 3 times the number of total deliveries can be readily achieved (FIG. 1).

In another embodiment of triplet delivery methods, a round of sequencing can be performed in which three different nucleotide monomers can be provided to a target nucleic acid in a delivery. In the next delivery, a plurality of nucleotide monomers, wherein at least one of the nucleotide monomers is different from each of the nucleotide monomers of the prior delivery can be provided to the target nucleic acid. This combination of deliveries can be repeated for a round of sequencing and sequence information of the target nucleic acid can be obtained. As discussed above, triplet delivery methods followed by delivery of a single nucleotide monomer that is different from each of the previously provided nucleotide monomers can produce sequence information relating to the position of a particular nucleotide monomer It will be appreciated that other combinations of nucleotide deliveries using nucleotide monomers can be used provided that the nucleotide monomers permit extension of a polynucleotide complementary to the target nucleic acid so as to obtain sequencing data. For example, the methods can employ a combination of several triplet deliveries, a combination of doublet and triplet deliveries, or a combination of singlet, doublet and triplet deliveries.

As will be apparent to the skilled artisan, the methods described herein have several significant applications. For example, methods described herein can be used to obtain long lengths of nucleic acid sequence at a low resolution and/or high resolution.

Methods to obtain long read lengths of sequence are an important tool in de novo genome sequencing. Sequencing massive lengths of genomic nucleic acids often requires the assembly of many shorter overlapping fragments of sequence into contigs. Difficulties in contig assembly can arise when short length reads of long homopolymer stretches of sequence must be assembled because it is difficult to accurately produce the homopolymer region from short sequences within the homopolymer region. Increasing the length of a contiguous sequencing read greatly reduces this problem by increasing the likelihood of producing fragments with sufficient sequence variation to permit homopolymer regions to be accurately assembled. Furthermore, long read lengths of sequence can provide scaffolds for the assembly of shorter fragments of sequence, obviating the need for many smaller sequences to contain overlapping sequences.

In addition, the long read lengths that can be obtained using the methods described herein can be used as a molecular DNA signature for applications involved in genotyping, expression profiling, for example, capturing alternative splicing, genome mapping, amplicon sequencing, and metagenomics.

It will be appreciated that in any of the methods described herein the order of sequencing reagent addition can be reversed. For example, in triplet delivery methods, a single nucleotide monomer can be provided in the first delivery of sequencing reagent. In the next delivery, the second sequencing reagent can comprise three nucleotide monomers that are different from the nucleotide monomer in the first sequencing reagent.

Furthermore, in some embodiments of the methods described herein, a first sequencing reagent can provide at least one type of nucleotide monomer. In such embodiments, a second sequencing reagent can contain at least two different nucleotide monomers. At least one of the at least two different nucleotide monomers of the second sequencing reagent can be different from the nucleotide monomer of the first sequencing reagent. In an exemplary embodiment, the first sequencing reagent can contain a single nucleotide monomer, for example, dATP, and the second sequencing reagent can contain three nucleotide monomers, for example, dCTP, dGTP, and dTTP.

Alternatively, other delivery combinations can be used. For example, a first sequencing reagent comprising one nucleotide monomer, followed by a second sequencing reagent comprising two of four different nucleotide monomers, followed by a third sequencing reagent comprising the remaining two of the four different nucleotide monomers is contemplated. As for other embodiments, the temporal order of additions is exemplary and other orders for delivering various combinations of nucleotides are also contemplated.

Target Nucleic Acids

A target nucleic acid can include any nucleic acid of interest. Target nucleic acids can include, but are not limited to, DNA, RNA, peptide nucleic acid, morpholino nucleic acid, locked nucleic acid, glycol nucleic acid, threose nucleic acid, mixtures thereof, and hybrids thereof In a preferred embodiment, genomic DNA fragments or amplified copies thereof are used as the target nucleic acid. In another preferred embodiment, mitochondrial or chloroplast DNA is used.

A target nucleic acid can comprise any nucleotide sequence. In some embodiment, the target nucleic acid comprises homopolymer sequences. A target nucleic acid can also include repeat sequences. Repeat sequences can be any of a variety of lengths including, for example, 2, 5, 10, 20, 30, 40, 50, 100, 250, 500, 1000 nucleotides or more. Repeat sequences can be repeated, either contiguously or non-contiguously, any of a variety of times including, for example, 2, 3, 4, 5, 6, 7, 8, 9, 10, 15, 20 times or more.

Some embodiments can utilize a single target nucleic acid. Other embodiments can utilize a plurality of target nucleic acids. In such embodiments, a plurality of target nucleic acids can include a plurality of the same target nucleic acids, a plurality of different target nucleic acids where some target nucleic acids are the same, or a plurality of target nucleic acids where all target nucleic acids are different. Embodiments that utilize a plurality of target nucleic acids can be carried out in multiplex formats such that reagents are delivered simultaneously to the target nucleic acids, for example, in a single chamber or on an array surface. In preferred embodiments, target nucleic acids can be amplified as described in more detail herein. In some embodiments, the plurality of target nucleic acids can include substantially all of a particular organism's genome. The plurality of target nucleic acids can include at least a portion of a particular organism's genome including, for example, at least about 1%, 5%, 10%, 25%, 50%, 75%, 80%, 85%, 90%, 95%, or 99% of the genome. In particular embodiments the portion can have an upper limit that is at most about 1%, 5%, 10%, 25%, 50%, 75%, 80%, 85%, 90%, 95%, or 99% of the genome Target nucleic acids can be obtained from any source. For example, target nucleic acids may be prepared from nucleic acid molecules obtained from a single organism or from populations of nucleic acid molecules obtained from natural sources that include one or more organisms. Sources of nucleic acid molecules include, but are not limited to, organelles, cells, tissues, organs, or organisms. Cells that may be used as sources of target nucleic acid molecules may be prokaryotic (bacterial cells, for example, *Escherichia, Bacillus, Serratia, Salmonella, Staphylococcus, Streptococcus, Clostridium, Chlamydia, Neisseria, Treponema, Mycoplasma, Borrelia, Legionella, Pseudomonas, Mycobacterium, Helicobacter, Erwinia, Agrobacterium, Rhizobium*, and *Streptomyces* genera); archeaon, such as crenarchaeota, nanoarchaeota or euryarchaeotia; or eukaryotic such as fungi, (for example, yeasts), plants, protozoans and other parasites, and animals (including insects (for example, *Drosophila* spp.), nematodes (for example, *Caenorhabditis elegan*), and mammals (for example, rat, mouse, monkey, non-human primate and human)).

Polymerases

The methods described herein can utilize polymerases. For example, polymerases can include, but are not limited to, DNA polymerases, RNA polymerases, reverse transcriptases, and mixtures thereof. The polymerase can be a thermostable polymerase or a thermodegradable polymerase. Examples of thermostable polymerases include polymerases isolated from *Thermus aquaticus, Thermus thermophilus, Pyrococcus woesei, Pyrococcus furiosus, Thermococcus litoralis, Bacillus stearothermophilus*, and *Thermotoga maritima*. Examples of thermodegradable polymerases include *E. coli* DNA polymerase, the Klenow fragment of *E. coli* DNA polymerase, T4 DNA polymerase, and T7 DNA polymerase. More examples of polymerases that can be used with the methods described herein include *E. coli*, T7, T3, and SP6 RNA polymerases, and AMV, M-MLV, and HIV reverse transcriptases. In some embodiments, the polymerase can have proofreading activity or other enzymic activities. Polymerases can also be engineered for example, to enhance or modify reactivity with various nucleotide analogs or to reduce an activity such as proofreading or exonuclease activity.

Sequencing Methods

The methods described herein can be used in conjunction with a variety of sequencing techniques. In some embodiments, the process to determine the nucleotide sequence of a target nucleic acid can be an automated process. Preferred embodiments include SBS techniques.

SBS techniques generally involve the enzymatic extension of a nascent nucleic acid strand through the iterative addition of nucleotides against a template strand. In traditional methods of SBS, a single nucleotide monomer may be provided to a target nucleotide in the presence of a polymerase in each delivery. However, in the methods described herein, more than one type of nucleotide monomer can be provided to a target nucleic acid in the presence of a polymerase in a delivery.

SBS can utilize nucleotide monomers that have a terminator moiety or those that lack any terminator moieties. Methods utilizing nucleotide monomers lacking terminators include, for example, pyrosequencing and sequencing using γ-phosphate-labeled nucleotides, as set forth in further detail below. In methods using nucleotide monomers lacking terminators, the number of nucleotides added in each cycle is generally variable and dependent upon the template sequence and the mode of nucleotide delivery. For SBS techniques that utilize nucleotide monomers having a terminator moiety, the terminator can be effectively irreversible under the sequencing conditions used as is the case for traditional Sanger sequencing which utilizes dideoxynucleotides, or the terminator can be reversible as is the case for sequencing methods developed by Solexa (now Illumina, Inc.).

SBS techniques can utilize nucleotide monomers that have a label moiety or those that lack a label moiety. Accordingly, incorporation events can be detected based on a characteristic of the label, such as fluorescence of the label; a characteristic of the nucleotide monomer such as molecular weight or charge; a byproduct of incorporation of the nucleotide, such as release of pyrophosphate; or the like. In embodiments, where two or more different nucleotides are present in a sequencing reagent, the different nucleotides can be distinguishable from each other, or alternatively, the two or more different labels can be the indistinguishable under the detection techniques being used. For example, the different nucleotides present in a sequencing reagent can have different labels and they can be distinguished using appropriate optics as exemplified by the sequencing methods developed by Solexa (now Illumina, Inc.). However, it is also possible to use the same label for the two or more different nucleotides present in a sequencing reagent or to use detection optics that do not necessarily distinguish the different labels. Thus, in a doublet sequencing reagent having a mixture of dATP/dCTP both the dATP and dCTP can be labeled with the same fluorophore. Furthermore, when doublet delivery methods are used all of the different nucleotide monomers can have the same label or different labels can be used, for example, to distinguish one mixture of different nucleotide monomers from a second mixture of nucleotide monomers. For example, using the [First delivery nucleotide monomers]+[Second delivery nucleotide monomers] nomenclature set forth above and taking an example of dATP/dCTP+dGTP/dTTP, the dATP and dCTP monomers can have the same first label and the dGTP and dTTP monomers can have the same second label, wherein the first label is different from the second label. Alternatively, the first label can be the same as the second label and incorporation events of the first delivery can be distinguished from incorporation events of the second delivery based on the temporal separation of cycles in an SBS protocol. Accordingly, a low resolution sequence representation obtained from such mixtures will be degenerate for two pairs of nucleotides (T/G, which is complementary to A and C, respectively; and C/A which is complementary to G/T, respectively).

Preferred embodiments include pyrosequencing techniques. Pyrosequencing detects the release of inorganic pyrophosphate (PPi) as particular nucleotides are incorporated into the nascent strand (Ronaghi, M., Karamohamed, S., Pettersson, B., Uhlen, M. and Nyren, P. (1996) "Real-time DNA sequencing using detection of pyrophosphate release." *Analytical Biochemistry* 242(1), 84-9; Ronaghi, M. (2001) "Pyrosequencing sheds light on DNA sequencing." *Genome Res.* 11(1), 3-11; Ronaghi, M., Uhlen, M. and Nyren, P. (1998) "A sequencing method based on real-time pyrophosphate." *Science* 281(5375), 363; U.S. Pat. No. 6,210,891; U.S. Pat. No. 6,258,568 and U.S. Pat. No. 6,274,320, the disclosures of which are incorporated herein by reference in their entireties). In pyrosequencing, released PPi can be detected by being immediately converted to adenosine triphosphate (ATP) by ATP sulfurylase, and the level of ATP generated is detected via luciferase-produced photons.

In another exemplary type of SBS, cycle sequencing is accomplished by stepwise addition of reversible terminator nucleotides containing, for example, a cleavable or photobleachable dye label as described, for example, in WO 04/018497 and U.S. Pat. No. 7,057,026, the disclosures of which are incorporated herein by reference. This approach is being commercialized by Solexa (now Illumina Inc.), and is also described in WO 91/06678 and WO 07/123744, each of which is incorporated herein by reference. The availability of fluorescently-labeled terminators in which both the termination can be reversed and the fluorescent label cleaved facilitates efficient cyclic reversible termination (CRT) sequencing. Polymerases can also be co-engineered to efficiently incorporate and extend from these modified nucleotides.

In accordance with the methods set forth herein, the two or more different nucleotide monomers that are present in a sequencing reagent or delivered to a template nucleic acid in the same cycle of a sequencing run need not have a terminator moiety. Rather, as is the case with pyrosequencing, several of the nucleotide monomers can be added to a primer in a template directed fashion without the need for an intermediate deblocking step. The nucleotide monomers can contain labels for detection, such as fluorescent labels, and can be used in methods and instruments similar to those commercialized by Solexa (now Illumina Inc.). Preferably in such embodiments, the labels do not substantially inhibit extension under SBS reaction conditions. However, the detection labels can be removable, for example, by cleavage or degradation. Removal of the labels after they have been detected in a particular cycle and prior to a subsequent cycle can provide the advantage of reducing background signal and crosstalk between cycles. Examples of useful labels and removal methods are set forth below.

In particular embodiments some or all of the nucleotide monomers can include reversible terminators. In such embodiments, reversible terminators/cleavable fluors can include fluor linked to the ribose moiety via a 3' ester linkage (Metzker, *Genome Res.* 15:1767-1776 (2005), which is incorporated herein by reference). Other approaches have separated the terminator chemistry from the cleavage of the fluorescence label (Ruparel et al., *Proc Natl Acad Sci USA* 102: 5932-7 (2005), which is incorporated herein by reference in its entirety). Ruparel et at described the development of reversible terminators that used a small 3' allyl group to block extension, but could easily be deblocked by a short treatment with a palladium catalyst. The fluorophore was attached to the base via a photocleavable linker that could easily be cleaved by a 30 second exposure to long wavelength UV light. Thus, either disulfide reduction or photocleavage can be used as a cleavable linker Another approach to reversible termination is the use of natural termination that ensues after placement of a bulky dye on a dNTP. The presence of a charged bulky dye on the dNTP can act as an effective terminator through steric and/or electrostatic hindrance. The presence of one incorporation event prevents further incorporations unless the dye is removed. Cleavage of the dye removes the fluor and effectively reverses the termination. Examples of modified nucleotides are also described in U.S. Pat. No. 7,427,673, and U.S. Pat. No. 7,057,026, the disclosures of which are incorporated herein by reference in their entireties.

Additional exemplary SBS systems and methods which can be utilized with the methods and systems described herein are described in U.S. Patent Application Publication No. 2007/0166705, U.S. Patent Application Publication No. 2006/0188901, U.S. Pat. No. 7,057,026, U.S. Patent Application Publication No. 2006/0240439, U.S. Patent Application Publication No. 2006/0281109, PCT Publication No. WO 05/065814, U.S. Patent Application Publication No. 2005/0100900, PCT Publication No. WO 06/064199 and PCT Publication No. WO 07/010251, the disclosures of which are incorporated herein by reference in their entireties.

Some embodiments can utilize sequencing by ligation techniques. Such techniques utilize DNA ligase to incorporate nucleotides and identify the incorporation of such nucleotides. Exemplary SBS systems and methods which can be utilized with the methods and systems described herein are described in U.S. Pat. No. 6,969,488, U.S. Pat. No. 6,172,218, and U.S. Pat. No. 6,306,597, the disclosures of which are incorporated herein by reference in their entireties.

Some embodiments can utilize nanopore sequencing (Deamer, D. W. & Akeson, M. "Nanopores and nucleic acids: prospects for ultrarapid sequencing." *Trends Biotechnol.* 18, 147-151 (2000); Deamer, D. and D. Branton, "Characterization of nucleic acids by nanopore analysis". *Acc. Chem. Res.* 35:817-825 (2002); Li, J., M. Gershow, D. Stein, E. Brandin, and J. A. Golovchenko, "DNA molecules and configurations in a solid-state nanopore microscope" *Nat. Mater.* 2:611-615 (2003), the disclosures of which are incorporated herein by reference in their entireties). In such embodiments, the target nucleic acid passes through a nanopore. The nanopore can be a synthetic pore or biological membrane protein, such as α-hemolysin. As the target nucleic acid passes through the nanopore, each base-pair can be identified by measuring fluctuations in the electrical conductance of the pore. (U.S. Pat. No. 7,001,792; Soni, G. V. & Meller, "A. Progress toward ultrafast DNA sequencing using solid-state nanopores." *Clin. Chem.* 53, 1996-2001 (2007); Healy, K. "Nanopore-based single-molecule DNA analysis." *Nanomed.* 2, 459-481 (2007); Cockroft, S. L., Chu, J., Amorin, M. & Ghadiri, M. R. "A single-molecule nanopore device detects DNA polymerase activity with single-nucleotide resolution." *J. Am. Chem. Soc.* 130, 818-820 (2008), the disclosures of which are incorporated herein by reference in their entireties).

Some embodiments can utilize methods involving the real-time monitoring of DNA polymerase activity. Nucleotide incorporations can be detected through fluorescence resonance energy transfer (FRET) interactions between a fluorophore-bearing polymerase and γ-phosphate-labeled nucleotides as described, for example, in U.S. Pat. No. 7,329,492 and U.S. Pat. No. 7,211,414 (each of which is incorporated herein by reference) or nucleotide incorporations can be detected with zero-mode waveguides as described, for example, in U.S. Pat. No. 7,315,019 (which is incorporated herein by reference) and using fluorescent nucleotide analogs and engineered polymerases as described, for example, in U.S. Pat. No. 7,405,281 and U.S. Patent Application Publication No. 2008/0108082 (each of which is incorporated herein by reference). The illumination can be restricted to a zeptoliter-scale volume around a surface-tethered polymerase such that incorporation of fluorescently labeled nucleotides can be observed with low background (Levene, M. J. et al. "Zero-mode waveguides for single-molecule analysis at high concentrations." *Science* 299, 682-686 (2003); Lundquist, P. M. et al. "Parallel confocal detection of single molecules in real time." *Opt. Lett.* 33, 1026-1028 (2008); Korlach, J. et al. "Selective aluminum passivation for targeted immobilization of single DNA polymerase molecules in zero-mode waveguide nanostructures." *Proc. Natl. Acad. Sci. USA* 105, 1176-1181 (2008), the disclosures of which are incorporated herein by reference in their entireties).

The above SBS methods can be advantageously carried out in multiplex formats such that multiple different target nucleic acids are manipulated simultaneously. In particular embodiments, different target nucleic acids can be treated in a common reaction vessel or on a surface of a particular substrate. This allows convenient delivery of sequencing reagents, removal of unreacted reagents and detection of incorporation events in a multiplex manner. In embodiments using surface-bound target nucleic acids, the target nucleic acids can be in an array format. In an array format, the target nucleic acids can be typically bound to a surface in a spatially distinguishable manner. The target nucleic acids can be bound by direct covalent attachment, attachment to a bead or other particle or binding to a polymerase or other molecule that is attached to the surface. The array can include a single copy of a target nucleic acid at each site (also referred to as a feature) or multiple copies having the same sequence can be present at each site or feature. Multiple copies can be produced by amplification methods such as, bridge amplification or emulsion PCR as described in further detail below.

The methods set forth herein can use arrays having features at any of a variety of densities including, for example, at least about 10 features/cm$^2$, 100 features/cm$^2$, 500 features/cm$^2$, 1,000 features/cm$^2$, 5,000 features/cm$^2$, 10,000 features/cm$^2$, 50,000 features/cm$^2$, 100,000 features/cm$^2$, 1,000,000 features/cm$^2$, 5,000,000 features/cm$^2$, or higher.

It will be appreciated that any of the above-described sequencing processes can be incorporated into the methods and/or systems described herein. For example, the methods or systems can utilize sequencing reagents having mixtures of two or more nucleotide monomers or can otherwise be carried out under conditions where two or more nucleotide monomers contact a target nucleic acid in a single sequencing cycle. Alternatively or additionally, the methods or systems set forth above can be used to obtain a sequence representation at single nucleotide resolution. As set forth in further detail below, a combination of sequence representations at low resolution and at single nucleotide resolution, can be advantageous for evaluating long sequences, for example, on a genome wide scale, for extending read length and/or for improving confidence in sequencing results via error checking Furthermore, it will be appreciated that other known sequencing processes can be easily by implemented for use with the methods and/or systems described herein.

Removing Nucleotide Monomers and/or Pyrophosphate

Some of the methods described herein include a step of removing a substance from a site. A site can include a site of nucleotide monomer incorporation and/or a site of detection of monomer incorporation. A substance can include, for example, any constituent of a sequencing reagent, any product of incorporating one or more nucleotide monomers into a polynucleotide complementary to a target nucleic acid, such as pyrophosphate, a target nucleic acid, a polymerase, a cleaved label, a polynucleotide complementary to a target nucleic acid. In a preferred embodiment, one or more nucleotide monomers are removed from a site. In another preferred embodiment, pyrophosphate is removed from a site. In even more preferred embodiments, both nucleotide monomers and pyrophosphate are removed from a site. Removing a substance can include a variety of methods, for example, washing a substance from a site, diluting a substance from a site, sequestering a substance from a site, degrading a substance, inactivating a substance and denaturing a substance.

In certain embodiments of the methods described herein, any portion of a substance can be removed from a site. In particular embodiments, approximately 1%, 5%, 10%, 20%, 30%, 40%, 50%, 60%, 70%, 80%, 90% and 95% of a substance can be removed from a site. In preferred embodiments, approximately 100% of a substance can be removed from a site.

In particular embodiments of the methods described herein, a portion of a sequencing reagent can be removed from a site of nucleotide monomer incorporation and/or a site of detection of monomer incorporation. A sequencing reagent can be removed from a site subsequent to providing the sequencing agent to a target nucleic acid in the presence of polymerase. In preferred embodiments, a sequencing reagent can be removed from a site before providing a subsequent sequencing reagent to a target nucleic acid in the presence of polymerase. In any of the above-described embodiments, the sequencing reagent can be the first, second, third, fourth, fifth or any subsequent sequencing reagent that is provided.

In some embodiments, an unincorporated nucleotide monomer can be removed from a site. In certain embodiments, an unincorporated nucleotide monomer can be removed from a site of nucleotide monomer incorporation and/or detection after providing the nucleotide monomer to a target nucleic acid. In more embodiments, an unincorporated nucleotide monomer can be removed from a site before providing a subsequent sequencing reagent to a target nucleic acid.

In some embodiments of the methods described herein, pyrophosphate can be removed from a site. In certain embodiments, pyrophosphate can be removed from a site of nucleotide monomer incorporation and/or detection after detecting incorporation one or more nucleotide monomers into a polynucleotide. In other embodiments, pyrophosphate can be removed from a site of nucleotide monomer incorporation and/or detection before providing a subsequent sequencing reagent to a target nucleic acid.

In some embodiments, a polynucleotide complementary to a target nucleic acid can be removed from a site. In certain embodiments, a polynucleotide complementary to a target nucleic acid can be removed from the target nucleic acid subsequent to performing a first run of sequencing on the target nucleic acid. In particular embodiments, a polynucleotide complementary to a target nucleic acid can be removed from the target nucleic acid before performing a second, third, or any subsequent run of sequencing on the target nucleic acid.

It will be understood that, in some embodiments, a substance can be removed from a site at any time before, during or subsequent to a round of sequencing.

Detection of Incorporated Nucleotide Monomers

Some of the methods described herein include a detection step for detecting the incorporation of nucleotide monomers into a polynucleotide. Nucleotide monomers may be incorporated into at least a portion of a polynucleotide complementary to the target nucleic acid. In certain embodiments, at least a portion of the sequencing reagent, which comprises unincorporated nucleotide monomers, may be removed from the site of incorporation/detection prior to detecting incorporated nucleotide monomers.

A variety of methods can be used to detect the incorporation of nucleotide monomers into a polynucleotide. In preferred methods, pyrophosphate released on incorporation of a nucleotide monomer into a polynucleotide can be detected using pyrosequencing techniques. As described above, pyrosequencing detects the release of pyrophosphate as particular nucleotides are incorporated into a nascent polynucleotide (Ronaghi, M., Karamohamed, S., Pettersson, B., Uhlen, M. and Nyren, P. (1996) "Real-time DNA sequencing using detection of pyrophosphate release." *Analytical Biochemistry* 242(1), 84-9; Ronaghi, M. (2001) "Pyrosequencing sheds light on DNA sequencing." *Genome Res.* 11(1), 3-11; Ronaghi, M., Uhlen, M. and Nyren, P. (1998) "A sequencing method based on real-time pyrophosphate." *Science* 281(5375), 363, the disclosures of which are incorporated herein by reference in their entireties).

In some embodiments, at least a portion of the ATP and non-incorporated nucleotides can be removed from the site of incorporation and/or detection. In preferred embodiments, the ATP and non-incorporated nucleotides can be removed subsequent to a detection step and prior to a delivery. Removing the ATP and non-incorporated nucleotides can include, for example, a washing step, and a degrading step using an enzyme such as apyrase (Ronaghi M, Karamohamed S, Pettersson B, Uhlen M, Nyren P. "Real-time DNA sequencing using detection of pyrophosphate release." *Analytical Biochemistry*. (1996) 242:84-89; Ronaghi M, Uhlen M, Nyren P. "A sequencing method based on real-time pyrophosphate." *Science* (1998) 281:363, the disclosures of which are hereby incorporated by reference in their entireties).

In some embodiments, at least a portion of released pyrophosphate can be removed from the site of incorporation and/or detection. In preferred embodiments, the released pyrophosphate can be removed subsequent to a detection step and prior to a delivery. In more embodiments, the released pyrophosphate can be removed prior to a delivery.

In more embodiments, incorporation of nucleotide monomers can be detected using nucleotide monomers comprising labels. Labels can include chromophores, enzymes, antigens, heavy metals, magnetic probes, dyes, phosphorescent groups, radioactive materials, chemiluminescent moieties, scattering or fluorescent nanoparticles, Raman signal generating moieties, and electrochemical detecting moieties. Such labels are known in the art some of which are exemplified previously herein or are disclosed, for example, in U.S. Pat. No. 7,052,839; Prober, et. al., *Science* 238: 336-41 (1997); Connell et. al., *BioTechniques* 5(4)-342-84 (1987); Ansorge, et. al., *Nucleic Acids Res.* 15(11): 4593-602 (1987); and Smith et. al., *Nature* 321:674 (1986), the disclosures of which are hereby incorporated by reference in their entireties. In preferred embodiments, a label can be a fluorophore. Exemplary embodiments include U.S. Pat. No. 7,033,764, U.S. Pat. No. 5,302,509, U.S. Pat. No. 7,416,844, and Seo et al. "Four color DNA sequencing by synthesis on a chip using photocleavable fluorescent nucleotides," *Proc. Natl. Acad. Sci. USA* 102: 5926-5931 (2005), which are herein incorporated by reference in their entireties.

Labels can be attached to the α, β, or γ phosphate, base, or sugar moiety, of a nucleotide monomer (U.S. Pat. No. 7,361, 466; Zhu et al., "Directly Labelled DNA Probes Using Fluorescent Nucleotides with Different Length Linkers," *Nucleic Acids Res.* 22: 3418-3422 (1994), and Doublie et al., "Crystal Structure of a Bacteriophage T7 DNA Replication Complex at 2.2 Å Resolution," *Nature* 391:251-258 (1998), which are hereby incorporated by reference in their entireties). Attachment can be with or without a cleavable linker between the label and the nucleotide.

In some embodiments, a label can be detected while it is attached to an incorporated nucleotide monomer. In such embodiments, unincorporated labeled nucleotide monomers can be removed from the site of incorporation and/or the site of detection prior to detecting the label.

Alternatively, a label can be detected subsequent to release from an incorporated nucleotide monomer. Release can be through cleavage of a cleavable linker, or on incorporation of the nucleotide monomer into a polynucleotide where the label is linked to the β or γ phosphate of the nucleotide monomer, namely, where released pyrophosphate is labeled.

In some embodiments, at least a portion of unincorporated labeled nucleotide monomers can be removed from the site of incorporation and/or detection. In preferred embodiments, at least a portion of unincorporated labeled nucleotide monomers can be removed prior to detecting the incorporated labeled nucleotide. In more preferred embodiments, approximately 50%, 60%, 70%, 80%, 90%, and 100% of unincorporated labeled nucleotide monomers can be removed prior to detecting the incorporated labeled nucleotide. In even more preferred embodiments, a label can be removed subsequent to a detection step and prior to a delivery. For example, a fluorescent label linked to an incorporated nucleotide monomer can be removed by cleaving the label from the nucleotide, or photobleaching the dye.

Exemplary embodiments of methods for detecting released labeled pyrophosphate include using nanochannels, using flowcells to separate and detect labeled pyrophosphate from unincorporated nucleotide monomers, and using mass spectroscopy (U.S. Pat. No. 7,361,466; U.S. Pat. No. 6,869,764; and U.S. Pat. No. 7,052,839, which are hereby incorporated by reference in their entireties). Released pyrophosphate may also be detected directly, for example, using sensors such as nanotubes (U.S. Patent Application Publication No. 2006/0, 199,193, which is hereby incorporated by reference in its entirety). In preferred embodiments, at least a portion of released pyrophosphate is removed from the site of incorporation and/or detection subsequent to the detection step and prior to a delivery. In more preferred embodiments, approximately 50%, 60%, 70%, 80%, 90%, 100% of released pyrophosphate is removed from the site of incorporation and/or detection subsequent to the detection step and prior to a delivery.

In some embodiments described herein, detection of the signal, such as light emitted form conversion of ATP and luciferin, or light emitted form a fluorescent label, is detected using a charge coupled device (CCD) camera. In other embodiments, a CMOS detector is used. Detection can occur on a CMOS array as described, for example, in Agah et al., "A High-Resolution Low-Power Oversampling ADC with Extended-Range for Bio-Sensor Arrays", *IEEE Symposium* 244-245 (2007) and Eltoukhy et al., "A 0.18 μm CMOS bioluminescence detection lab-on-chip", *IEEE Journal of Solid-State Circuits* 41: 651-662 (2006), the disclosures of which are incorporated herein by reference in their entireties. In addition, it will be appreciated that other signal detecting devices as known in the art can be used to detect signals produced as a result of nucleotide monomer incorporation into a polynucleotide complementary to a target nucleic acid.

Variable Resolution Sequencing of Target Nucleic Acids

Some embodiments described herein include methods for obtaining long sequence reads with high resolution sequence data for a portion of a target nucleic acid in one or more single sequencing runs (rounds of sequencing). A portion of a target nucleic acid can include any portion of a target nucleic acid, for example, approximately 1%, 5%, 10%, 20%, 30%, 40%, 50%, 60%, 70%, 80%, 90%, 95% or, 99%. In certain embodiments, a portion of a target nucleic acid can include a contiguous sequence. A contiguous portion can be measured as a percentage of a larger fragment as above or in terms of the number of nucleotides sequenced. For example, the portion can be about 10, 20, 30, 40, 50, 100, 150, 200, 250 or 500 nucleotides or more. Alternatively, a portion of a target nucleic can include a plurality of non-contiguous sequences. For example, a portion of a target nucleic acid can include two ends of a target nucleic acid. Typically the two ends are the same length, but they need not be and the two ends of a larger fragment that are sequenced at high resolution can differ in length. Again, each end can have a length that is measured as a percentage of the larger fragment, including for example, the percentages listed above or as a number of nucleotides including, for example, the numbers listed above.

In certain methods, a sequencing run can comprise more than one series of nucleotide monomer delivery steps in which the number of nucleotide monomers can vary. For example, a sequencing run can include a series of single nucleotide monomer delivery steps to yield high resolution sequence information, and also include a series of multiple nucleotide monomer delivery steps to yield low resolution sequence information. It will be understood that a sequencing run can include any combination of nucleotide monomer delivery step, for example, single, doublet, or triplet delivery steps. In many embodiments, conditions can be used that result in longer extension lengths for the cycles that are carried out with a series of multiple nucleotide monomer delivery steps compared to the extension lengths resulting from single nucleotide monomer delivery steps.

In an exemplary embodiment, a sequencing run can include a series of consecutive single nucleotide delivery steps where dATP, dCTP, dGTP, and dTTP are each provided to a target nucleic acid in subsequent delivery steps. Such delivery steps can yield sequence information at high resolution. The sequencing run can also include a series of consecutive doublet delivery steps where, for example, dATP/dCTP are supplied in a single delivery step, and dGTP/dTTP are supplied in a subsequent delivery steps. Such delivery steps can yield long lengths of sequence information, albeit at a lower resolution.

Several cycles can be carried out using single nucleotide delivery steps, followed by several cycles where a sequencing reagent having several different nucleotide types is delivered, and then followed by several cycles of single nucleotide delivery steps. Such methods can be used as a means to provide sequence of a target nucleic acid, wherein the sequence obtained at each end of the target nucleic acid is of high resolution and the sequence obtained from the middle portion is at a lower resolution. Although the exact nucleotide sequence of the middle, low resolution portion is not known, the number of nucleotide monomer incorporation events in this portion can be determined. As such, the approximate length of the combined sequenced portion of the target nucleic acid (both high resolution and lower resolution sequence portions) can be determined. The sequence of the middle portion need not be determined at single nucleotide resolution. Furthermore, the high resolution end portion sequences of the target nucleic acid can be used to enhance assembly, for example, of long homopolymer regions. Methods for assembling a long sequence, such as a genome, from paired-end sequences of several fragments thereof are known in the art and can be applied to the methods set forth herein. Exemplary methods are described in WO 2007/010252, WO 2008/041002, U.S. Patent Application Publication No. 2006/0024681, and U.S. Patent Application Publication No. 2006/0292611, each of which is incorporated herein by reference. In this way, high sequence resolution methodology can be employed when determining accurate nucleotide sequence is important and low resolution methodology can be employed when extending the sequence read length is valuable but knowledge of the sequence of the target nucleic acid region that is sequenced is not important.

High Resolution Sequence Acquisition Via Multiple Rounds of Low Resolution Sequencing Nucleic acid sequence information can be obtained from two or more rounds of low resolution sequencing carried out on the same target nucleic acid. A first low resolution sequence representation can be obtained for a target nucleic acid, using methods set forth herein. The first low resolution sequence representation can be degenerate with respect to two or more nucleotide types. As exemplified in the upper chart of FIG. 2, a first predicted sequence obtained from cycles of sequencing using mixtures of A/C and G/T is degenerate with respect to two pairs of nucleotide types, G/T and A/C. Following the first round of low resolution sequencing, the products of the first round can be removed leaving the target nucleic acid in condition for a second round of sequencing. A second low resolution sequence representation for the target nucleic acid can be obtained using similar methods except that at least one of the two or more nucleotide types in the first low resolution sequence representation is different from at least one of the two or more nucleotide types in the second low resolution sequence representation. Looking again to FIG. 2, the middle chart is exemplary of a second predicted sequence obtained from cycles of sequencing using mixtures of A/G and C/T, resulting in a low resolution sequence that is degenerate with respect to C/T and A/G. The two low resolution sequences can be compared to determine the actual sequence of the target nucleic acid at single nucleotide resolution as shown in the lower chart of FIG. 2. Mixtures of nucleotide monomers can be used additionally or alternatively to those exemplified above including, for example, various doublet mixtures or triplet mixtures such as those set forth elsewhere herein.

The above methods can be carried out for a plurality of target nucleic acids, for example, in a multiplex format. In such embodiments, multiple low resolution sequence representations can be associated with individual target nucleic acid molecules and used to determine the actual sequence of the target nucleic acid at single nucleotide resolution. Taking an array format as an example, a plurality of first low resolution sequence representations can be obtained after a first round of sequencing, each of the low resolution sequence representations being associated with known features on the array. Following the first round of low resolution sequencing the array can be treated, for example using denaturing conditions to remove extension products of the first round of sequencing and to return the single stranded target nucleic acids at each feature to a state that is ready for a second round of sequencing. Then a plurality of second low resolution sequence representations can be obtained from a second round of sequencing, each of the low resolution sequence representations being associated with known features on the array. By comparing the two low resolution sequence representations at each feature, the actual sequence of the target nucleic acid at each feature can be determined at single nucleotide resolution.

In particular embodiments, low resolution sequence representations can be obtained for a plurality of target nucleic acids that are fragments of a larger nucleic acid such as a genome. In such embodiments, the sequence information for the individual fragments can be used to determine the actual sequence of the larger nucleic acid at single nucleotide resolution. For example, multiple low resolution sequence representations from each feature can be used to determine the actual sequence of each fragment target nucleic acid at single nucleotide resolution. The actual sequence of each fragment can then be used to determine the actual sequence of the larger sequence, for example, by alignment to a reference sequence or by de novo assembly methods. In an alternative embodiment, the low resolution sequence representations from different features can be used directly to determine the actual sequence of the larger sequence, for example, using pattern matching methods.

Low resolution sequence representations can provide a signature for different nucleic acids in a sample. Accordingly, the actual sequence of a target nucleic acid need not be determined at single-nucleotide resolution and, instead, a low resolution sequence representation of the nucleic acid can be used. In particular embodiments, a low resolution sequence representation can be used to determine the presence or absence of a target nucleic acid in a particular sample or to quantify the amount of the target nucleic acid. Exemplary applications include, but are not limited to, expression analysis, identification of organisms, or evaluation of structure for chromosomes, expressed RNAs or other nucleic acids as set forth in further detail below.

In particular embodiments, low resolution sequence representations for one or more target mRNA molecules can be used to determine expression levels in one or more samples of interest. So long as the low resolution sequence representations are sufficiently indicative of the mRNA, the actual sequence need not be known at single nucleotide resolution. For example, if a low resolution sequence representation distinguishes a target mRNA from all other mRNA species expressed in a target sample and in a reference sample, then comparison of the low resolution sequence representations from both samples can be used to determine relative expression levels. Target nucleic acids used in expression methods can be obtained from any of a variety of different samples including, for example, cells, tissues or biological fluids from organisms such as those set forth above. Presence or absence, or even quantities of target nucleic acids can be determined for samples that have been treated with different chemical agents, physical manipulations, environmental conditions or the like. Alternatively or additionally, samples can be from organisms that are experiencing any of a variety of diseases, conditions, developmental states or the like. Typically, a reference sample and target sample will differ in regard to one or more of the above factors (for example, treatment, conditions, species origin, or cell type).

In particular embodiments, low resolution sequence representations for target nucleic acids obtained from a particular organism can be used to characterize or identify the organism. For example, a pathogenic organism can be identified in an environmental sample or in a clinical sample from an individual based on at least one low resolution sequence representation for a target nucleic acid from the sample. So long as the one or more low resolution sequence representations are sufficiently indicative of the organism, the actual sequence need not be known at single nucleotide resolution. For example, if a low resolution sequence representation distinguishes a pathogenic bacterial strain from other bacteria, then comparison of the low resolution sequence representations from the sample of interest to low resolution sequence representations from reference samples or from a database can be used to detect presence or absence of the pathogenic bacterial strain.

In further embodiments, the structure of a chromosome, RNA or other nucleic acid can be determined based on low resolution sequence representations. For example, if a low resolution sequence representation distinguishes a chromosomal region from other regions of a chromosome, then comparison of the low resolution sequence representations from a target sample and a reference sample for which the chromosome structure is known can be used to identify insertions, deletions or rearrangements in the target sample. Similarly, if a low resolution sequence representation distinguishes a target mRNA isoform (i.e. alternative splice product of a gene) from another mRNA isoform expression product of the same gene, then comparison of the low resolution sequence representations for both isoforms can be used to determine presence or absence of the target isoform. Target nucleic acids used to determine chromosome or RNA structure can be obtained from any of a variety of samples including, but not limited to those exemplified above.

In some embodiments, one or more steps are carried out by a computer. For example, low resolution sequence representations can be provided to a computer that is programmed to compare representations to each other, determine an actual sequence of a target nucleic acid at single nucleotide resolution, identify samples from which a low resolution sequence representation was derived or the like. Exemplary computer systems that are useful in the invention include, but are not limited to personal computer systems, such as those based on Intel®, IBM®, or Motorola® microprocessors; or work stations such as a SPARC workstation or UNIX workstation. Useful systems include those using the Microsoft Windows, UNIX or LINUX operating system. The systems and methods described herein can also be implemented to run on client-server systems or wide-area networks such as the Internet.

A computer system useful in the invention can be configured to operate as either a client or server and can include one or more processors which are coupled to a random access memory (RAM). Implementation of embodiments of the present invention is not limited to any particular environment or device configuration. The embodiments of the present invention may be implemented in any type of computer system or processing environment capable of supporting the methodologies which are set forth herein. In particular embodiments, algorithms can be written in MATLAB, C or C++, or other computer languages known in the art.

The computer can be further programmed to store one or more of the representations and the actual sequence. The computer can be programmed to transmit one or more of the representations, the actual sequence or other relevant information to a user, another computer, a database or a network. The computer can also be programmed to receive relevant information from a user, another computer, a database or a network. Such information can include data, such as signals or images, obtained from a sequencing method, one or more reference sequences, characteristics of an organism of interest or the like.

Preparation of Amplified Target Nucleic Acids

In some embodiments, a target nucleic acid can be amplified for use with the methods described herein. Such embodiments include preparing amplified libraries of target nucleic acids. Library preparation can be accomplished by random fragmentation of DNA, followed by in vitro ligation of common adaptor sequences.

Various protocols can be used to generate an array of millions of spatially immobilized PCR colonies, sometimes referred to as polonies, on a substrate. For example, such clonally clustered amplicons of target nucleic acids can be generated by in situ polonies, emulsion PCR, or bridge PCR (Mitra, R. D. & Church, G. M. "In situ localized amplification and contact replication of many individual DNA molecules." *Nucleic Acids Res.* 27, e34 (1999); Dressman, D., Yan, H., Traverso, G., Kinzler, K. W. & Vogelstein, B. "Transforming single DNA molecules into fluorescent magnetic particles for detection and enumeration of genetic variations." *Proc. Natl. Acad. Sci. USA* 100, 8817-8822 (2003); Adessi, C. et al. "Solid phase DNA amplification: characterisation of primer attachment and amplification mechanisms." *Nucleic Acids Res.* 28, e87 (2000); Fedurco, M., Romieu, A., Williams, S., Lawrence, I. & Turcatti, G. "BTA, a novel reagent for DNA attachment on glass and efficient generation of solid-phase amplified DNA colonies." *Nucleic Acids Res.* 34, e22 (2006), each of which is incorporated by reference herein in their entireties).

In embodiments using emulsion PCR, an in vitro-constructed adaptor flanked shotgun library can be PCR amplified in a water-in-oil emulsion. The PCR is multi-template PCR, because only a single primer pair is used. One of the PCR primers is tethered to the surface (5'-attached) of micron-scale beads that are also included in the reaction. A low template concentration results in most bead-containing compartments having either zero or one template molecule present. In productive emulsion compartments (where both a bead and template molecule is present), PCR amplicons can be captured to the surface of the bead. After breaking the emulsion, beads bearing amplification products can be selectively enriched. Each clonally amplified bead will bear on its surface PCR products corresponding to amplification of a single molecule from the template library. Various embodiments of emulsion PCR methods that are useful are set forth in U.S. Patent Application Publication No. 2005/0042648; U.S. Patent Application Publication No. 2005/0079510; U.S. Patent Application Publication No. 2005/0130173 and WO 05/010145, each of which is incorporated herein by reference.

In embodiments using bridge PCR, also known as cluster PCR, an in vitro-constructed adaptor-flanked shotgun library can be PCR amplified using primers coated densely on the surface of a substrate. The primers are attached at their 5' ends by a flexible linker. Amplification products originating from any given member of the template library remain locally tethered near the point of origin. At the conclusion of the PCR, each clonal cluster contains ~1,000 copies of a single member of the template library. Accurate measurement of the concentration of the template library can be used to optimize the cluster density while simultaneously avoiding overcrowding. Various embodiments of bridge PCR methods that are useful are set forth in U.S. Patent Application Publication No. 2007/0128624, WO 07/010251, U.S. Pat. No. 6,090,592 and U.S. Pat. No. 5,641,658, each of which is incorporated herein by reference.

Such embodiments, can generate PCR amplicons derived from any given single library molecule that are spatially separated, for example, at discrete sites or features on a planar substrate (in situ polonies, bridge PCR), or to the surface of micron-scale beads, which can be recovered and arrayed (emulsion PCR).

Clusters in Wells

More techniques that can used with the methods described herein include the preparation of substrates with target nucleic acids and/or enzymes attached to the surface of substrate. In some embodiments, the substrate comprises one or more wells. Such embodiments are especially advantageous, in pyroseqeuncing where the shape and depth of the wells can be optimized for fluidic delivery of reagents between detection steps, and for reducing diffusion of pyrophosphate during detection steps.

In an exemplary embodiment, modified primers and enzymes can be attached to the surface of wells by coating the wells with a linking compound, for example activated dextran. The dextran can be activated by including groups that are reactive to amines, for example, aldehyde. The surface of the wells can be reacted with amino modified primers, for example, a primer P1 and a primer P2. Such primers can be used for bridge PCR at the surface of the well. In addition, the surface of the wells can be reacted with peptides having a biotin moiety. The biotin moiety can be used to an intermediary coupling agent, for example, a streptavidin agent. Biotinylated enzymes can be attached to the surface of the well through the intermediary coupling agent. Wells having target nucleic acids and/or enzymes attached thereto, can be used with the methods described herein. As will be appreciated, the amount of primers and enzymes on the well surface can be optimized by various methods, including for example, by optimizing the density of reactants on the surface of the wells.

Cluster Formation by Re-Seeding

Additional techniques that can be used with the methods described herein include processes for increasing the number of wells or other features on a substrate that contain clusters. In many SBS applications, substrate features or wells may not be efficiently used because many of the features or wells lack a target nucleic acid. The process described below, which is termed reseeding, can include the steps of (1) seeding the substrate with a target nucleic acid, (2) performing limited cycles of bridge amplification on the target nucleic acid, and (3) re-seeding the substrate with the target nucleic acid and repeating the amplification step. In some embodiments, several cycles of re-seeding can be used to further increase the number of wells containing target nucleic acids.

In an exemplary embodiment, a substrate comprises a plurality of wells wherein the wells further comprise attached primers, namely, primer P1 and primer P2. P1 and P2 can hybridize to adapter sequences present on a sample comprising a plurality of different target nucleic acids. In a first seeding, the target nucleic acids can be seeded to the substrate in a diffuse concentration such that each well may be seeded with a single target nucleic acid only. Accordingly, many of the wells may not be occupied with a target nucleic acid.

Bridge amplification can be carried out for a limited number of cycles, for example, 5-15 cycles. Each well with a target nucleic acid is likely to contain a plurality of amplified target nucleic acid, for example, 30-50 target nucleic acid molecules.

In a second seeding, the substrate can be re-seeded with the sample comprising a plurality of different target nucleic acids, in a diffuse concentration such that each well may be seeded from the sample with a single target nucleic acid only. More wells will now be seeded with a single target nucleic acid, however, some of the wells that were previously seeded and amplified may contain more than one type target nucleic acid.

Bridge amplification can be repeated for a limited number of cycles, for example, 5-15 cycles. Under these conditions, more wells will have been newly seeded with target single target nucleic acids and will yield a uniform population of template copies.

Wells that were seeded in the first and second seedings may contain a large amount of the first seeded target nucleic acid, and a much lower amount of the second seeded target nucleic acid. The seeding step and bridge amplification step can be repeated, for example, one or more times, so that it is likely that a well will contain a single target nucleic acid or a small amount of an additional target nucleic acid.

The conditions for number of cycles for seeding the wells and bridge amplification, and the number of cycles for bridge amplification can be optimized such the additional target nucleic acid in a well containing more than one type of target nucleic acid is unlikely to be amplified to a level that adversely affects the signal-to-noise ratio in sequencing reactions.

Some embodiments of the above-described processes can be applied to substrates that do not comprise wells. For example, substrates having a surface with a contiguous reactive surface capable of attaching to several spatially separated molecules of interest (or colonies of molecules of interest). An exemplary substrate is a Solexa flow cell. However, the re-seeding methods provide particular advantageous in embodiments using substrates with a patterned surface of features, for example, a surface which may comprise one or more reactive pads or wells. Substrates having features that are spatially separated in a repeated or otherwise ordered pattern may be desired over large contiguous surfaces to which different molecules are randomly deposited to form features. For example, a relatively high density of features can be provided in the case of the former while reducing the probability, on one hand, of overlapping features which can occur in the case of the latter when the surface is too densely populated, and, on the other hand, the probability of unused space in the case of the latter when the surface is too diffusely populated. Also, the presence of a non-random pattern can make detection more efficient in some embodiments by easing resource requirements for accurate image registration and precise pinpointing of information content on the surface. Re-seeding can allow a larger fraction of the features on a patterned surface to be occupied compared to other methods of depositing molecules of interest only once.

EXAMPLES

Example 1

Single, Doublet and Triplet Delivery Methods

Single Delivery Method

Using a pyrosequencing methodology, in a first flow step, a sequencing reagent comprising dATP is provided to a target nucleic acid in the presence of polymerase. If dATP is incorporated into the polynucleotide complementary to the target nucleic acid, a signal proportional to the number of incorporated units of nucleotide monomers is produced and detected. Subsequent to this flow step unincorporated dATP is washed away.

In a second flow step, a sequencing reagent comprising dCTP is provided to a target nucleic acid in the presence of polymerase. If dCTP is incorporated into the polynucleotide complementary to the target nucleic acid, a signal proportional to the number of incorporated units of nucleotide monomers is produced and detected. Subsequent to this flow step unincorporated dCTP is washed away.

In a third flow step, a sequencing reagent comprising dGTP is provided to a target nucleic acid in the presence of polymerase. If dGTP is incorporated into the polynucleotide complementary to the target nucleic acid, a signal proportional to the number of incorporated units of nucleotide monomers is produced and detected. Subsequent to this flow step unincorporated dGTP is washed away.

In a fourth flow step, a sequencing reagent comprising dTTP is provided to a target nucleic acid in the presence of polymerase. If dTTP is incorporated into the polynucleotide complementary to the target nucleic acid, a signal proportional to the number of incorporated units of nucleotide monomers is produced and detected. Subsequent to this flow step unincorporated dTTP is washed away.

The first, second, third and fourth flow, detection and wash steps are repeated for a total of 500 deliveries. For the round of sequencing, sequence information of the target nucleic acid is obtained. A read length of less than 300 base pairs is obtained (FIG. 1).

Doublet Delivery Method

Using a pyrosequencing methodology, in a first flow step, a sequencing reagent comprising dATP and dCTP is provided to a target nucleic acid in the presence of polymerase. If dATP and/or dCTP are incorporated into the polynucleotide complementary to the target nucleic acid, a signal proportional to the number of incorporated units of nucleotide monomers is produced and detected. Subsequent to this flow step unincorporated dATP and dCTP are washed away.

In a second flow step, a sequencing reagent comprising dGTP and dTTP is provided to the target nucleic acid. If dGTP and/or dTTP are incorporated into the polynucleotide complementary to the target nucleic acid, a signal proportional to the number of incorporated units of nucleotide monomers is produced and detected. Subsequent to this flow step unincorporated dGTP and dTTP are washed away.

The first and second flow, detection, and wash steps are repeated for a total of 500 deliveries. For the round of sequencing, sequence information of the target nucleic acid is obtained. A read length of approximately 900 base pairs is obtained (FIG. 1).

Triplet Delivery Method

Using a pyrosequencing methodology, in a first flow step, a sequencing reagent comprising dATP, dCTP, and dGTP is provided to a target nucleic acid in the presence of polymerase. If dATP, dCTP, and/or dGTP are incorporated into the polynucleotide complementary to the target nucleic acid, a signal proportional to the number of incorporated units of nucleotide monomers is produced and detected. Subsequent to this flow step unincorporated dATP, dCTP, and/or dGTP are washed away.

In a second flow step, a sequencing reagent comprising dTTP is provided to a target nucleic acid in the presence of polymerase. If dTTP is incorporated into the polynucleotide complementary to the target nucleic acid, a signal proportional to the number of incorporated units of nucleotide monomers is produced and detected. Subsequent to this flow step unincorporated dTTP is washed away.

The first and second flow, detection and wash steps are repeated for a total of 500 deliveries. For the round of sequencing, sequence information of the target nucleic acid is obtained. A read length of approximately 1650 base pairs is obtained (FIG. 1).

In some alternative embodiments, nucleotide monomers used in a previous flow step are incorporated in subsequent flow steps. In other embodiments, it is possible to change the composition of the first and/or second sequencing reagent before the end of the sequencing run. The following example provides an illustration of each of these alternatives applied to a single sequencing round.

In a first flow step, a sequencing reagent comprising dATP, dCTP, and dGTP is provided to a target nucleic acid in the presence of polymerase. If dATP, dCTP, and/or dGTP are incorporated into the polynucleotide complementary to the target nucleic acid, a signal proportional to the number of incorporated units of nucleotide monomers is produced and detected. Subsequent to this flow step unincorporated dATP, dCTP, and/or dGTP are washed away.

In a second flow step, a sequencing reagent comprising dATP, dCTP, and dTTP is provided to a target nucleic acid in the presence of polymerase. If dATP, dCTP, and/or dTTP are incorporated into the polynucleotide complementary to the target nucleic acid, a signal proportional to the number of incorporated units of nucleotide monomers is produced and detected. Subsequent to this flow step unincorporated dATP, dCTP, and/or dTTP are washed away.

In a third flow step, a sequencing reagent comprising dATP, dGTP, and dTTP is provided to a target nucleic acid in the presence of polymerase. If dATP, dGTP, and/or dTTP are incorporated into the polynucleotide complementary to the target nucleic acid, a signal proportional to the number of incorporated units of nucleotide monomers is produced and detected. Subsequent to this flow step unincorporated dATP, dGTP, and/or dTTP are washed away.

In a fourth flow step, a sequencing reagent comprising dCTP, dGTP, and dTTP is provided to a target nucleic acid in the presence of polymerase. If dCTP, dGTP, and/or dGTP are incorporated into the polynucleotide complementary to the target nucleic acid, a signal proportional to the number of incorporated units of nucleotide monomers is produced and detected. Subsequent to this flow step unincorporated dCTP, dGTP, and/or dTTP are washed away.

The first, second, third and fourth flow, detection and wash steps are repeated for a total of 500 deliveries. For the round of sequencing, sequence information of the target nucleic acid is obtained. A read length of approximately 1650 base pairs is obtained (FIG. 1).

Example 2

High Resolution Sequencing of a Target Nucleic Acid

This example demonstrates a method of obtaining high resolution sequence information using a doublet delivery process. This example is illustrated in FIG. 2. To begin, a first round of sequencing is performed on a target nucleic acid using a doublet delivery method according to Example 1 and as shown in the upper chart of FIG. 2. The first flow step includes providing a first sequencing reagent comprising dATP and dCTP to the target nucleic acid. A 1× signal intensity is detected in the first cycle, indicative of a single nucleotide monomer incorporation. The second flow step includes providing a second sequencing reagent comprising dGTP and dTTP to the target nucleic acid. A 2× signal intensity is detected in the second cycle, indicative of two nucleotide monomer incorporations. The first and second flow, detection, and wash steps are repeated for a total of 8 cycles. For the first round of sequencing, a $1^{st}$ predicted sequence of the target nucleic acid is obtained. Accordingly a low resolution sequence representation covering a read length of 12 base pairs is obtained.

In the next round of the high resolution sequencing process, the polynucleotide complementary to the target nucleic acid is removed. A second round of sequencing is then performed on the target nucleic acid using a doublet delivery method according to Example 1 except the starting doublet combination is changed as shown in the middle chart of FIG. 2. For example, in the second round, the first flow step includes providing a first sequencing reagent comprising dATP and dGTP to the target nucleic acid. A 3× signal intensity is detected in the first cycle, indicative of three nucleotide monomer incorporations. The second flow step includes providing a second sequencing reagent comprising dCTP and dTTP to the target nucleic acid. A 2× signal intensity is detected in the second cycle, indicative of two nucleotide monomer incorporations. The first and second flow, detection, and wash steps are repeated for a total of 6 cycles. For the second round of sequencing, a $2^{nd}$ predicted sequence of the target nucleic acid is obtained. Accordingly low resolution sequence representation covering a read length of 12 base pairs is obtained.

Sequence information from the first and second rounds of sequencing is combined and a high resolution sequence of the target nucleic acid is obtained as shown in the lower chart of FIG. 2.

Example 3

High/Low Resolution Sequencing of Target Nucleic Acids

In some applications, for example, in paired end sequencing, it can be advantageous to obtain long lengths of sequence information at a lower resolution, while obtaining sequence information for the flanking ends of the target nucleic acid at a higher resolution. In some applications, a combination of delivery methods can be applied in a round of sequencing.

In a round of sequencing, a single delivery method and a triplet delivery method are applied to obtain high resolution sequence information for 100 bp of each end of a 1500 bp target nucleic acid. A single delivery method is applied to obtain sequencing information for the first 100 bp of the target nucleic acid, then a triplet delivery method is applied to obtain sequence information for the next 1300 bp of the target nucleic acid, then a single delivery method is applied to obtain sequence information for final 100 base pairs of the 1500 bp target nucleic acid.

The above description discloses several methods and systems of the present invention. This invention is susceptible to modifications in the methods and materials, as well as alterations in the fabrication methods and equipment. Such modifications will become apparent to those skilled in the art from a consideration of this disclosure or practice of the invention disclosed herein. For example, the invention has been exemplified using nucleic acids but can be applied to other polymers as well. Consequently, it is not intended that this invention be limited to the specific embodiments disclosed herein, but that it cover all modifications and alternatives coming within the true scope and spirit of the invention.

All references cited herein including, but not limited to, published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

The term "comprising" as used herein is synonymous with "including," "containing," or "characterized by," and is inclusive or open-ended and does not exclude additional, unrecited elements or method steps.

What is claimed is:

1. A method of making an array of nucleic acid colonies, comprising
   (a) providing a substrate comprising a patterned surface of features, wherein the features are spatially separated from each other on the surface of the substrate;
   (b) contacting the substrate with a solution of different target nucleic acids to seed a subset of the features that contact the solution, wherein each feature in the subset is seeded with a single nucleic acid from the solution, wherein a plurality of the features that contact the solution are not seeded with a nucleic acid from the solution;
   (c) amplifying the nucleic acids to form a nucleic acid colony at each of the features in the subset; and
   (d) repeating steps (b) and (c) to increase the number of the features on the surface that comprise a nucleic acid colony, thereby making an array of nucleic acid colonies.

2. The method of claim 1, further comprising detecting the array of nucleic acid colonies in a sequencing reaction.

3. The method of claim 2, wherein a subset of the colonies in the array comprise a first type of target nucleic acid and a second type of target nucleic acid.

4. The method of claim 3, wherein the amount of the second type of target nucleic acid does not adversely affect the signal-to-noise for the detecting of the first type of nucleic acid.

5. The method of claim 2, wherein the detecting comprises detecting a byproduct of incorporating a nucleotide into a nucleic acid.

6. The method of claim 5, wherein the byproduct is pyrophosphate.

7. The method of claim 2, wherein the sequencing reaction comprises extension of a nascent nucleic acid strand through iterative addition of nucleotides against templates in the nucleic acid colonies.

8. The method of claim 7, wherein the nucleotides comprise fluorescent labels that are detected in the sequencing reaction.

9. The method of claim 1, wherein the features comprise wells.

10. The method of claim 1, wherein the features comprise attached primer nucleic acids for the amplifying.

11. The method of claim 10, wherein each of the features comprises a pair of attached primer nucleic acids.

12. The method of claim 11, wherein the amplifying comprises bridge amplification.

13. The method of claim 10, wherein the amplifying comprises polymerase chain reaction amplification.

14. The method of claim 10, wherein the nucleic acid colonies are covalently attached to the features.

15. The method of claim 1, wherein the features comprise reactive pads on the surface.

16. The method of claim 1, wherein the patterned surface comprises a repeated pattern of the features.

17. The method of claim 1, wherein the same solution of different target nucleic acids is contacted with the substrate in steps (b) and (d).

18. The method of claim 1, wherein the substrate comprises a CMOS detector.

19. The method of claim 1, wherein the substrate comprises a density of at least 1,000 features/cm$^2$.

* * * * *

SEQUENCE LISTING

```
<160> NUMBER OF SEQ ID NOS: 3

<210> SEQ ID NO 1
<211> LENGTH: 12
<212> TYPE: DNA
<213> ORGANISM: Artificial Sequence
<220> FEATURE:
<223> OTHER INFORMATION: Illustrative Example

<400> SEQUENCE: 1
tccgactagg ca                                                          12

<210> SEQ ID NO 2
<211> LENGTH: 12
<212> TYPE: DNA
<213> ORGANISM: Artificial Sequence
<220> FEATURE:
<223> OTHER INFORMATION: Illustrative Example

<400> SEQUENCE: 2
kmmkmmkmkk mm                                                          12

<210> SEQ ID NO 3
<211> LENGTH: 12
<212> TYPE: DNA
<213> ORGANISM: Artificial Sequence
```

```
<220> FEATURE:
<223> OTHER INFORMATION: Illustrative Example

<400> SEQUENCE: 3
yyyrryyrrr yr                                                    12
```